(12) United States Patent
Bhushan et al.

(10) Patent No.: US 10,405,777 B2
(45) Date of Patent: Sep. 10, 2019

(54) APPARATUSES, SYSTEMS AND METHODS FOR DETECTION OF AN INGESTED BATTERY OR MAGNET

(71) Applicant: Northwestern University, Evanston, IL (US)

(72) Inventors: Bharat Bhushan, Chicago, IL (US); Claus-Peter Richter, Skokie, IL (US); Jonathan Ida, Chicago, IL (US)

(73) Assignees: Northwestern University, Evanston, IL (US); Ann and Robert H. Lurie Children's Hospital of Chicago, Chicago, IL (US)

( * ) Notice: Subject to any disclaimer, the term of this patent is extended or adjusted under 35 U.S.C. 154(b) by 87 days.

(21) Appl. No.: 15/830,214

(22) Filed: Dec. 4, 2017

(65) Prior Publication Data

US 2018/0242880 A1   Aug. 30, 2018

Related U.S. Application Data

(60) Provisional application No. 62/430,209, filed on Dec. 5, 2016.

(51) Int. Cl.
*G01R 33/00* (2006.01)
*A61B 5/06* (2006.01)
*G01R 33/07* (2006.01)
*G01V 3/08* (2006.01)

(52) U.S. Cl.
CPC .......... *A61B 5/062* (2013.01); *G01R 33/0023* (2013.01); *G01R 33/07* (2013.01); *G01V 3/081* (2013.01); *A61B 2560/0223* (2013.01)

(58) Field of Classification Search
CPC  A61B 5/062; A61B 2560/0223; G01V 3/081; G01R 33/0023; G01R 33/07
USPC ........................................ 324/251, 244, 200
See application file for complete search history.

(56) References Cited

U.S. PATENT DOCUMENTS

| | | | |
|---|---|---|---|
| 2010/0033204 A1* | 2/2010 | Santo ................. | G01R 31/2879 324/750.05 |
| 2012/0126820 A1* | 5/2012 | Tan ...................... | G01R 31/386 324/434 |
| 2012/0224433 A1* | 9/2012 | Mochida ............ | G01R 31/2856 365/185.27 |

* cited by examiner

*Primary Examiner* — Giovanni Astacio-Oquendo
(74) *Attorney, Agent, or Firm* — Nancy R. Gamburd; Gumburd Law Group LLC

(57) ABSTRACT

Representative apparatus, method, and system embodiments are disclosed for non-invasive detection an ingested battery or magnet in a human or other animal subject. The various apparatus embodiments include one or more Hall effect sensors, arranged in a hand-held embodiment or arranged along a flexible strip having an adhesive. A calibration may be determined or reference or calibration field measurements may be generated. A flexible strip is arranged, or the hand-held embodiment is moved, over the esophagus of the subject to generate target magnetic field measurements. The presence of an ingested battery or magnet is detected when one or more target magnetic field measurements (or gradient) is or are greater than or equal to a first predetermined threshold, or when a sign reversal occurs for a difference between target and reference measurements. The various apparatus and system embodiments may also include a monitor for signal processing and display of results.

43 Claims, 26 Drawing Sheets

RISK OF BUTTON BATTERIES

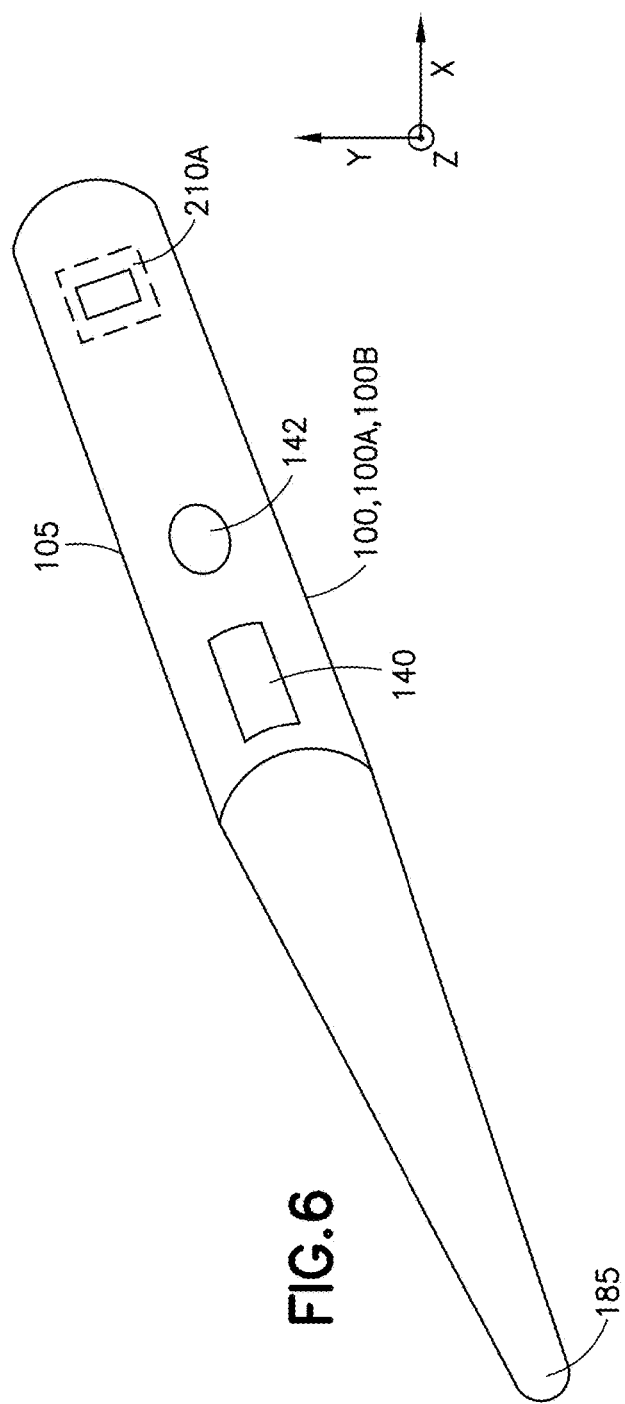
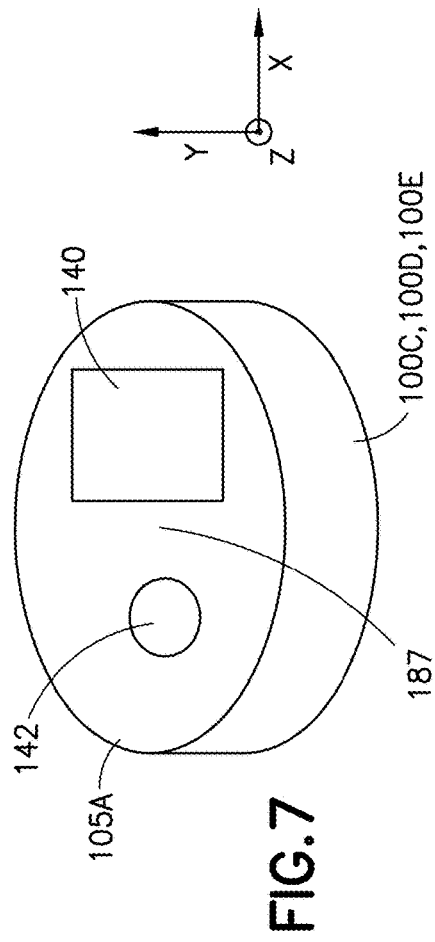

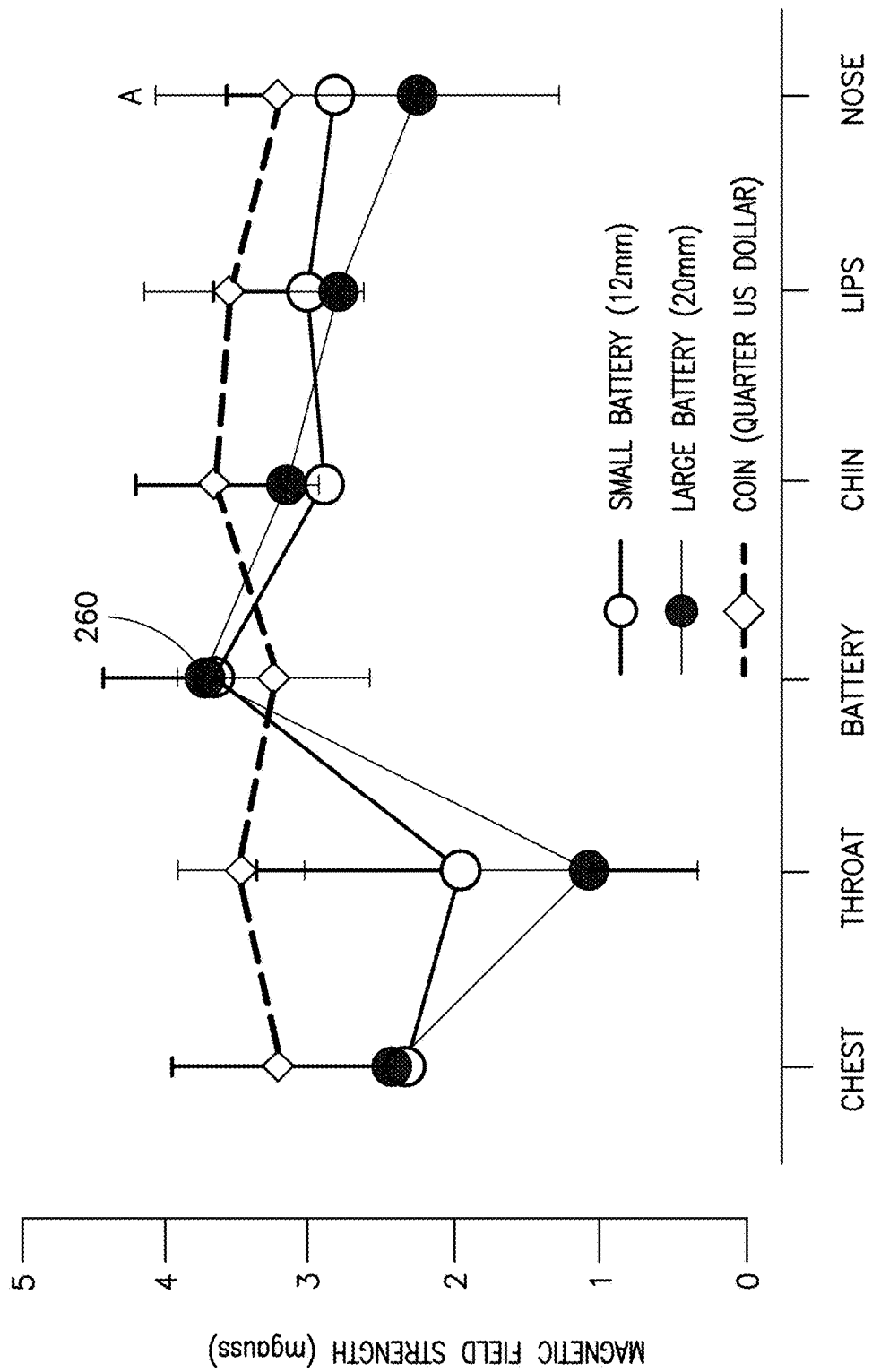

APPARATUSES, SYSTEMS AND METHODS FOR DETECTION OF AN INGESTED BATTERY OR MAGNET

CROSS-REFERENCE TO A RELATED APPLICATION

This application is a nonprovisional of and claims the benefit of and priority to U.S. Provisional Patent Application No. 62/430,209, filed Dec. 5, 2016, inventors Bharat Bhushan et al., titled "Apparatus, System and Method for Detection of an Ingested Battery or Magnet", which is commonly assigned herewith, and all of which is hereby incorporated herein by reference in its entirety with the same full force and effect as if set forth in its entirety herein.

FIELD OF THE INVENTION

The present invention, in general, relates to detection of an ingested foreign object, and more particularly, relates to apparatuses, systems and methods for noninvasive detection of an ingested battery or magnet.

BACKGROUND OF THE INVENTION

Ingestion of a foreign body can be a life-threating event. This is the case if the foreign body blocks the airway and leads to suffocation and quick death of the patient.

Other objects that do not block the airway still can interfere with the transport of matter along the digestive tract and might block the passage of food with subsequent complications. Foreign body ingestion in children, moreover, is a common problem, with coins being the most commonly ingested.

With the modern age and an increasing number of battery-operated toys and controls in the household, another complication can arise: the ingestion of a battery. With increasing accessibility to electronic toys and devices by children, however, more batteries have been swallowed and affected children required medical attention by pediatricians and pediatric otolaryngologists (Marom et al., 2010). In many cases, the batteries pass the upper gastrointestinal tract and are eliminated in the stool after a few days.

This is different in small children such as young children, toddlers and infants, however, especially for those who are too young to adequately inform a parent or treating physician concerning the nature of what the child may have ingested. Batteries with a 12 mm or larger diameter can become impacted in the esophagus and an electrical current can form around the outside of the battery. This generates hydroxide and cause serious internal injuries, tissue damage, chemical burns, and even death (Marom et al., 2010). An example of the burning effects of a battery are shown in FIG. 1. In rare cases, ensuing damage may include esophageal or an aortic perforation, tracheo-esophageal fistula, severe esophageal bleeding, vocal cord paralysis, and heavy metal poisoning or intoxication.

A study by Litovitz et al. (2010) summarizes the most important trend in 2010. The authors examined data from, the (1) National Poison Data System (56535 cases, 1985-2009), (2) the National Battery Ingestion Hotline (8648 cases, July 1990-September 2008) and (3) the medical literature and the National Battery Ingestion Hotline cases (13 deaths and 73 major outcomes). All sources showed worsening outcomes, with a 6.7-fold increase in the percentage of button battery ingestions with major or fatal outcomes from 1985 to 2009 (National Poison Data System). The ingestions of 20- to 25-mm-diameter cells increased from 1% to 18% of ingested button batteries (1990-2008). This is similar to the rise in ingestion of lithium cell batteries (1.3% to 24%). The reported outcomes were significantly worse when the batteries were large-diameter lithium cell batteries ($\geq 20$ mm) and the children were younger than 4 years old. The 20-mm lithium cell batteries were implicated in the most severe outcomes. Severe burns with sequelae occurred in just 2 to 2.5 hours. Most fatal (92%) or major outcome (56%) ingestions were not witnessed. At least 27% of major outcome and 54% of fatal cases were misdiagnosed, usually because of nonspecific presentations. Injuries may also continue after removal of the battery, with unanticipated and delayed esophageal perforations, tracheoesophageal fistulas, fistulization into major vessels, and massive hemorrhage.

Typical prior art procedures to be followed for a patient with foreign body ingestion is shown in FIGS. 2-4. FIG. 2 illustrates a typical foreign body evaluation worksheet. It should be noted that high-risk scenarios include button batteries located in the esophagus, lead objects located in the stomach, and magnets and metal objects located in the stomach and beyond. Since batteries may cause severe damage (including death of a child) in under two to 2.5 hours, it is extremely important that any ingested battery be identified as such very early in the medical examination process.

In case that a battery has been ingested, another diagnostic and treatment worksheet is typically followed, as illustrated in the flow chart of FIG. 3. It should be noted that impacted button batteries in the esophagus of children is an emergency. The therapeutic procedure is the removal of the battery with rigid esophaguscopy or bronchoscopy. Additional treatments may also be provided following the removal of the battery.

Similarly to ingestion of batteries, ingestion of magnets creates an emergency situation as well. A diagnostic and treatment worksheet exists for magnetic ingestion, as illustrated in the flow chart of FIG. 4. Many magnets are made of materials which are toxic. In addition, in the event more than one magnet is ingested, or ingested along with other ferromagnetic or magnetic objects such as pins or coins, the multiple magnets and/or other objects may clamp around tissue in the gastrointestinal (GI) tract, causing myriad problems such as puncture wounds, other perforations, or impactions, also requiring immediate removal of the magnet (s). All of these situations may also be life threatening and/or may significantly increase the duration of hospitalization of a child, resulting in increased healthcare costs.

In addition to ingestion of a battery or a magnet by a child, batteries or magnets may also be ingested by a pet, such as a pet dog or cat, resulting in a veterinary emergency, with similar procedures utilized to diagnose and treat the affected animal.

X-ray imaging is often utilized to determine if an ingested object is a battery, a coin, or another object. Moreover, several x-rays may have to be taken to clearly distinguish between a battery and a non-battery foreign body. In many instances, however, x-ray imaging cannot discriminate between objects such as button batteries or coins. For example, a button battery cannot be distinguished from a coin in an x-ray image when a double shadow or "halo" sign of a battery is not discernable in the image. An example of an x-ray image allowing the identification of a button battery is shown in FIG. 5, which shows the double shadow or halo 30 of a button battery 50. In many cases, moreover, especially as button batteries become increasingly thinner, and a double shadow or halo may not be discernable in imaging. In addition, in circumstances or locations which do not have an x-ray machine readily available, and/or available within a comparatively short window of time, an ingested foreign body cannot be identified as a battery, magnet or coin. In other cases it is not possible to immediately take an x-ray, such as in a physician office or at the child's home.

Accordingly, it is extremely important to identify an ingested foreign object as a battery or a magnet to appropriately treat the child or pet and to minimize side effects that can result from battery or magnet ingestion, such as the severe burning from a battery illustrated in FIG. 1.

Accordingly, there is an ongoing need for new apparatuses, methods and/or systems for noninvasive and accurate detection of an ingested battery or magnet. Such an apparatus, method and/or system should be comparatively unobtrusive, portable, convenient and easy to use for a treating physician, a nurse, a technician, other medical personnel, or an individual consumer, while nonetheless being comparatively or sufficiently accurate to obtain meaningful results and actionable information, and with a comparatively fast detection time.

REFERENCES

Bruzzi, J. F., Munden, R. F., Truong, M. T., Marom, E. M., Sabloff, B. S., Gladish, G. W., Iyer, R. B., Pan, T. S., Macapinlac, H. A., Erasmus, J. J. 2007. PET/CT of esophageal cancer: its role in clinical management. Radiographics 27, 1635-52.

Kokia, E. S., Marom, R., Shalev, V., Jan, Y., Shemer, J. 2006. The use of medical informatics as a management tool for community health services during the 2006 Israel-Lebanon War. Isr Med Assoc J 8, 865-9.

Kramer, R. E., Lerner, D. G., Lin, T., Manfredi, M., Shah, M., Stephen, T. C., Gibbons, T. E., Pall, H., Sahn, B., McOmber, M., Zacur, G., Friedlander, J., Quiros, A. J., Fishman, D. S., Mamula, P., North American Society for Pediatric Gastroenterology, H., Nutrition Endoscopy, C. 2015. Management of ingested foreign bodies in children: a clinical report of the NASPGHAN Endoscopy Committee. J Pediatr Gastroenterol Nutr 60, 562-74.

Litovitz, T., Whitaker, N., Clark, L., White, N. C., Marsolek, M. 2010. Emerging battery-ingestion hazard: clinical implications. Pediatrics 125, 1168-77.

Marom, T., Goldfarb, A., Russo, E., Roth, Y. 2010. Battery ingestion in children. Int J Pediatr Otorhinolaryngol 74, 849-54.

Patz, E. F., Jr., Erasmus, J. J., McAdams, H. P., Connolly, J. E., Marom, E. M., Goodman, P. C., Leder, R. A., Keogan, M. T., Herndon, J. E. 1999. Lung cancer staging and management: comparison of contrast-enhanced and nonenhanced helical CT of the thorax. Radiology 212, 56-60.

Pitaro, J., Bechor-Fellner, A., Gavriel, H., Marom, T., Eviatar, E. 2016. Sudden sensorineural hearing loss in children: Etiology, management, and outcome. Int J Pediatr Otorhinolaryngol 82, 34-7.

Zadik, Y., Marom, Y., Levin, L. 2009. Dental practitioners' knowledge and implementation of the 2007 International Association of Dental Traumatology guidelines for management of dental trauma. Dent Traumatol 25, 490-3.

SUMMARY OF THE INVENTION

As discussed in greater detail below, the representative apparatus, system and method provide for noninvasive detection of an ingested battery or magnet. The representative apparatus and system are comparatively unobtrusive, portable, convenient and easy to use for a treating physician, a nurse, a technician, other medical personnel, or an individual consumer, while nonetheless being comparatively or sufficiently accurate to obtain meaningful results and actionable information, with a comparatively fast detection time.

A representative system embodiment is disclosed for detection of an ingested battery or magnet, with the representative system comprising: a detection apparatus comprising: a plurality of Hall effect sensors to generate a corresponding plurality of Hall effect voltage signals; and an amplifier coupled to the plurality of Hall effect sensors to amplify the plurality of Hall effect voltage signals, and generate at least one first amplified Hall effect voltage signal provided as a calibration or reference magnetic field measurement and generate a second plurality of amplified Hall effect voltage signals provided as target magnetic field measurements.

In a representative embodiment, the system may further comprise: a monitor comprising: an analog-to-digital converter to receive the at least one first amplified Hall effect voltage signal and the second plurality of amplified Hall effect voltage signals and respectively convert the first amplified Hall effect voltage signal and second plurality of amplified Hall effect voltage signals to a corresponding calibration or reference magnetic field digital value and to corresponding target magnetic field digital values; and a processor coupled to the analog-to-digital converter, the processor adapted to compare one or more target magnetic field digital values with a first predetermined threshold, and when one or more target magnetic field digital values is greater than or equal to the first predetermined threshold, to generate a detection signal indicating the presence of an ingested battery or magnet.

In a representative embodiment, the processor may be further adapted to compare the one or more target magnetic field digital values with the first predetermined threshold and with a second predetermined threshold, and when one or more target magnetic field digital values is greater than or equal to the first predetermined threshold and less than the second predetermined threshold, to generate a detection signal indicating the presence of an ingested battery.

In a representative embodiment, the processor may be further adapted, when one or more target magnetic field digital values is greater than or equal to the second predetermined threshold, to generate a detection signal indicating the presence of an ingested magnet.

In a representative embodiment, the processor may be further adapted to use at least one maximum or gradient of the one or more target magnetic field digital values to compare the one or more target magnetic field digital values with the first predetermined threshold.

In a representative embodiment, the system may be portable. In another representative embodiment, the monitor may have a hand-held form factor. In another representative embodiment, the monitor is embodied in a computer, a tablet computer, or a smartphone.

In another representative embodiment, the system may further comprise: a monitor comprising: an analog-to-digital converter to receive the at least one first amplified Hall effect voltage signal and the second plurality of amplified Hall effect voltage signals and respectively convert the first amplified Hall effect voltage signal and second plurality of amplified Hall effect voltage signals to a corresponding calibration or reference magnetic field digital value and to corresponding target magnetic field digital values; and a processor coupled to the analog-to-digital converter, the processor adapted to determine one or more differences between the corresponding calibration or reference magnetic field digital value and the target magnetic field digital values, and when at least one difference has a sign reversal, to generate a detection signal indicating the presence of an ingested battery or magnet.

In a representative embodiment, the detection apparatus may further comprise: a filter coupled to the plurality of Hall effect sensors and to the amplifier to filter the plurality of Hall effect voltage signals; and a housing having a hand-held, generally cylindrical or disc-shaped form factor; and wherein the plurality of Hall effect sensors are arranged near a tip or center of the housing.

In another representative embodiment, the detection apparatus may further comprise: a filter coupled to the plurality of Hall effect sensors and to the amplifier to filter the plurality of Hall effect voltage signals; and a housing comprising: a flexible material layer; and an adhesive coupled to the flexible material layer.

In another representative embodiment, the detection apparatus may further comprise: a thermal sensor.

A representative method of using such a system for detection of an ingested battery or magnet in a human or animal subject is also disclosed, comprising: moving or positioning the detection apparatus along a first region anterior to the esophagus of the subject to generate the target magnetic field measurements at one or more first locations; and moving or positioning the detection apparatus in a second region spaced-apart from the first region, to generate the one or more calibration or reference magnetic field measurements at one or more second locations.

Another representative method of using such a system for detection of an ingested battery or magnet in a human or animal subject is also disclosed, comprising: moving the detection apparatus along a first region anterior to the esophagus of the subject to generate the target magnetic field measurements at one or more first locations; and calibrating the detection apparatus in a second region spaced-apart from the first region, to generate the one or more calibration or reference magnetic field measurements at one or more second locations.

Another representative apparatus embodiment is also disclosed for detection of an ingested battery or magnet, with the representative apparatus comprising: at least one Hall effect sensor to generate a plurality of Hall effect voltage signals; an amplifier coupled to the at least one Hall effect sensor to amplify the plurality of Hall effect voltage signals, and generate at least one first amplified Hall effect voltage signal provided as a calibration or reference magnetic field measurement and generate a second plurality of amplified Hall effect voltage signals provided as target magnetic field measurements; an analog-to-digital converter to receive the first amplified Hall effect voltage signal and the second pluralities of amplified Hall effect voltage signals and respectively convert the first amplified Hall effect voltage signal and second plurality of amplified Hall effect voltage signals to a corresponding calibration or reference magnetic field digital value and corresponding target magnetic field digital values; and a processor coupled to the analog-to-digital converter, the processor adapted to compare one or more target magnetic field digital values with a first predetermined threshold, and when one or more target magnetic field digital values is greater than or equal to the first predetermined threshold, to generate a detection signal indicating the presence of an ingested battery or magnet.

In a representative embodiment, the processor may be further adapted to compare the one or more target magnetic field digital values with the first predetermined threshold and with a second predetermined threshold, and when one or more target magnetic field digital values is greater than or equal to the first predetermined threshold and less than the second predetermined threshold, to generate a detection signal indicating the presence of an ingested battery. In a representative embodiment, the processor may be further adapted, when one or more target magnetic field digital values is greater than or equal to the second predetermined threshold, to generate a detection signal indicating the presence of an ingested magnet. In a representative embodiment, the processor may be further adapted to use at least one maximum or gradient of the one or more target magnetic field digital values to compare the one or more target magnetic field digital values with the first predetermined threshold.

In a representative embodiment, the apparatus may further comprise: a filter coupled to the at least one Hall effect sensor and to the amplifier to filter the plurality of Hall effect voltage signals; and a housing having a hand-held, generally cylindrical form factor and wherein the plurality of Hall effect sensors are arranged near a tip of the housing.

In another representative embodiment, the apparatus may further comprise: a filter coupled to the at least one Hall effect sensor and to the amplifier to filter the plurality of Hall effect voltage signals; and a housing having a hand-held, disc-shaped form factor and wherein the plurality of Hall effect sensors are arranged near a center of the housing.

In another representative embodiment, the apparatus may further comprise: a thermal sensor.

A representative method of using such an apparatus for detection of an ingested battery or magnet in a human or animal subject is also disclosed, comprising: moving the detection apparatus along a first region anterior to the esophagus of the subject to generate the target magnetic field measurements at one or more first locations; and moving the detection apparatus in a second region spaced-apart from the first region, to generate one or more calibration or reference magnetic field measurements at one or more second locations.

Another representative method of using such an apparatus for detection of an ingested battery or magnet in a human or animal subject is also disclosed, comprising: moving the detection apparatus along a first region anterior to the esophagus of the subject to generate the target magnetic field measurements at one or more first locations; and calibrating the detection apparatus in a second region spaced-apart from the first region, to generate one or more calibration or reference magnetic field measurements at one or more second locations.

Another representative system embodiment is disclosed for detection of an ingested battery or magnet, with the representative system comprising:

a first detection apparatus comprising: a first flexible strip having an adhesive film; a first plurality of Hall effect sensors to generate a corresponding first plurality of Hall effect voltage signals, the first plurality of Hall effect sensors arranged as a linear array on or within the first flexible strip; and a first amplifier coupled to the first plurality of Hall effect sensors to amplify the first plurality of Hall effect voltage signals and generate a first plurality of amplified Hall effect voltage signals provided as reference magnetic field measurements; and a second detection apparatus comprising: a second flexible strip having an adhesive film; a second plurality of Hall effect sensors to generate a corresponding second plurality of Hall effect voltage signals, the second plurality of Hall effect sensors arranged as a linear array on or within the second flexible strip; and a second amplifier coupled to the second plurality of Hall effect sensors to amplify the second plurality of Hall effect voltage signals and generate a second plurality of amplified Hall effect voltage signals provided as target magnetic field measurements.

In a representative embodiment, each of the first and second detection apparatuses may further comprise: a filter coupled to the first or second plurality of Hall effect sensors and to the first or second amplifier to filter the first or second plurality of Hall effect voltage signals; and an input-output connector.

In another representative embodiment, each of the first and second detection apparatuses may further comprise: a filter coupled to the first or second plurality of Hall effect sensors and to the first or second amplifier to filter the first or second plurality of Hall effect voltage signals; and a wireless interface circuit.

In a representative embodiment, the system may further comprise: a monitor comprising: an analog-to-digital converter to receive the first and second pluralities of amplified Hall effect voltage signals and respectively convert the first and second pluralities of amplified Hall effect voltage signals to corresponding calibration or reference magnetic field digital values and target magnetic field digital values; and a processor coupled to the analog-to-digital converter, the processor adapted to compare one or more target magnetic field digital values with a first predetermined threshold, and when one or more target magnetic field digital values is greater than or equal to the first predetermined threshold, to generate a detection signal indicating the presence of an ingested battery or magnet.

In a representative embodiment, the processor may be further adapted to compare the one or more target magnetic field digital values with the first predetermined threshold and with a second predetermined threshold, and when one or more target magnetic field digital values is greater than or equal to the first predetermined threshold and less than the second predetermined threshold, to generate a detection signal indicating the presence of an ingested battery.

In a representative embodiment, the processor may be further adapted, when one or more target magnetic field digital values is greater than or equal to the second predetermined threshold, to generate a detection signal indicating the presence of an ingested magnet.

In a representative embodiment, the processor may be further adapted to use at least one maximum or gradient of the one or more target magnetic field digital values to compare the one or more target magnetic field digital values with the first predetermined threshold.

In a representative embodiment, the system may be portable. In another representative embodiment, the monitor may have a hand-held form factor. In another representative embodiment, the monitor is embodied in a computer, a tablet computer, or a smartphone.

In another representative embodiment, the system may further comprise: a monitor comprising: an analog-to-digital converter to receive the first and second pluralities of amplified Hall effect voltage signals and respectively convert the first and second pluralities of amplified Hall effect voltage signals to corresponding calibration or reference magnetic field digital values and target magnetic field digital values; and a processor coupled to the analog-to-digital converter, the processor adapted to determine one or more differences between the corresponding calibration or reference magnetic field digital value and the target magnetic field digital values, and when at least one difference has a sign reversal, to generate a detection signal indicating the presence of an ingested battery or magnet.

A representative method of using such a system for detection of an ingested battery or magnet in a human or animal subject is also disclosed, comprising: arranging the second detection apparatus in a first region anterior to the esophagus of the subject; arranging the first detection apparatus laterally and spaced-apart from the second detection apparatus in a second region along the chest or side of the subject; and providing power to the first and second detection apparatuses to generate the first and second pluralities of Hall effect voltage signals.

A non-invasive method of detecting an ingested battery or magnet in a human or animal subject is also disclosed, with the method comprising: moving an apparatus having at least one Hall effect sensor along a first region of the subject to generate target magnetic field measurements at one or more first locations; calibrating the apparatus spaced apart from the first region or moving the apparatus in a second region of the human subject to generate reference magnetic field measurements at one or more second locations; comparing one or more target magnetic field measurements with a first predetermined threshold; and detecting the presence of an ingested battery or magnet when one or more target magnetic field digital values is greater than or equal to the first predetermined threshold.

In a representative embodiment, the method may further comprise: comparing the one or more target magnetic field digital values with the first predetermined threshold and with a second predetermined threshold; and detecting the presence of an ingested battery when one or more target magnetic field digital values is greater than or equal to the first predetermined threshold and less than the second predetermined threshold, to generate a detection signal indicating the presence of an ingested battery.

In a representative embodiment, the method may further comprise: detecting the presence of an ingested when one or more target magnetic field digital values is greater than or equal to the second predetermined threshold.

In a representative embodiment, the method may further comprise: determining at least one maximum or gradient of the one or more target magnetic field digital values; and comparing the at least one maximum or gradient with the first predetermined threshold.

In a representative method embodiment, the first region is anterior to the esophagus of the human subject. For example, the first region may extend between the tip of the chin to the xiphoid process of the subject. In a representative method embodiment, the second region is lateral to and spaced-apart from the first region. For example, the second region may be along the chest or side of the subject.

Numerous other advantages and features of the present invention will become readily apparent from the following detailed description of the invention and the embodiments thereof, from the claims and from the accompanying drawings.

BRIEF DESCRIPTION OF THE DRAWINGS

The objects, features and advantages of the present invention will be more readily appreciated upon reference to the following disclosure when considered in conjunction with the accompanying drawings, wherein like reference numerals are used to identify identical components in the various views, and wherein reference numerals with alphabetic characters are utilized to identify additional types, instantiations or variations of a selected component embodiment in the various views, in which:

FIG. 6 is an isometric diagram illustrating a first representative, hand-held battery and magnet detection apparatus embodiment.

FIG. 7 is an isometric diagram illustrating a second representative, hand-held battery and magnet detection apparatus embodiment.

FIG. 26 is a graphical diagram illustrating magnetic field measurements taken from three human cadavers after a battery or a coin (as a reference object) was inserted in the esophagus.

FIG. 27 is a bar chart illustrating magnetic field measurements taken from three human cadavers after a battery or a coin (as a reference object) was inserted in the esophagus.

DETAILED DESCRIPTION OF REPRESENTATIVE EMBODIMENTS

Figure 1:
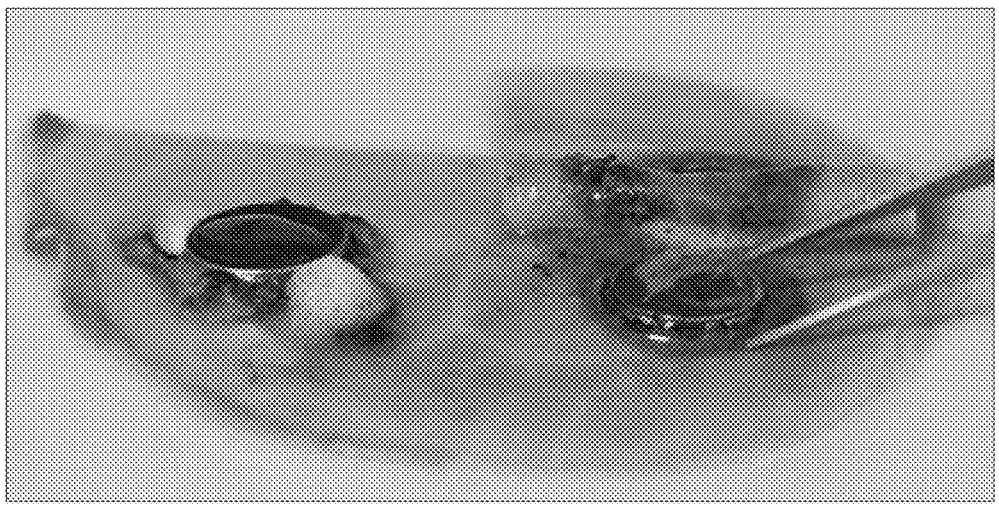
FIG. 1 is a photograph (available at http://www.bbc.com/news/health-37410343) illustrating tissue damage and chemical burn effects of a battery placed on moist muscle tissue.
Figure 2:
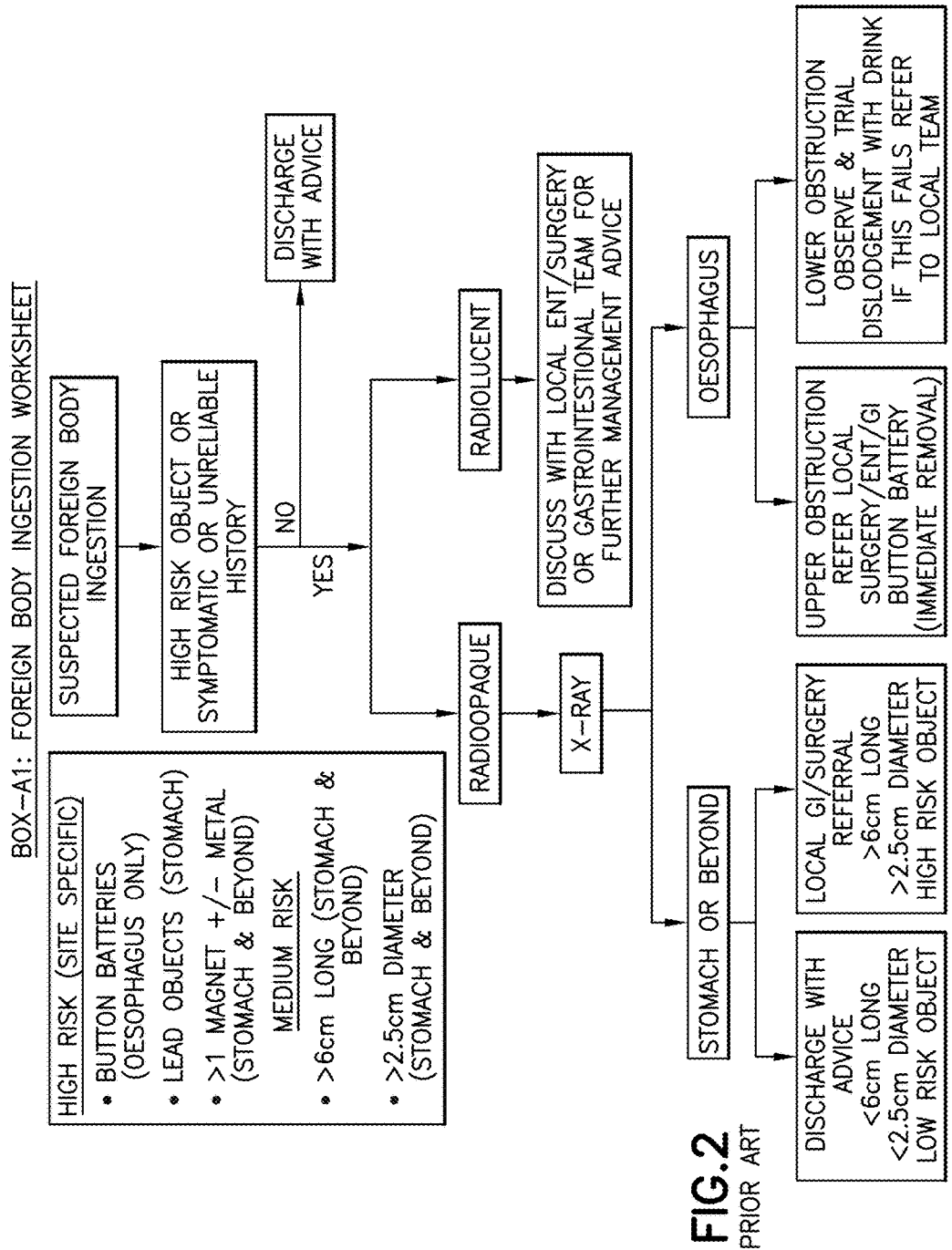
FIG. 2 is a prior art flow chart illustrating a typical foreign body ingestion evaluation worksheet (available at http://www.rch.org.au/clinicalguide/guideline index/Foreign Body Ingestion/).
Figure 3:
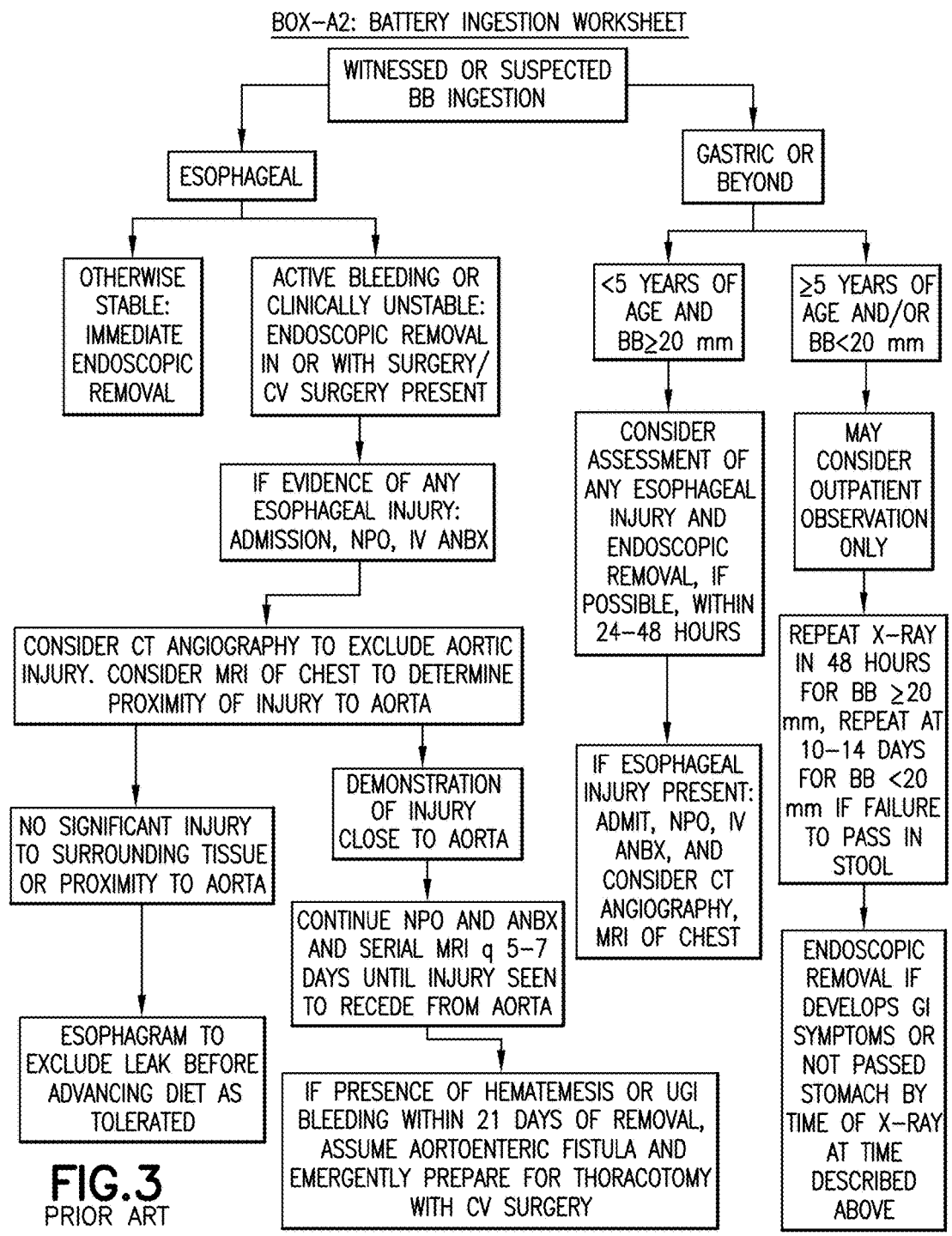
FIG. 3 is a prior art flow chart illustrating a typical battery ingestion worksheet (available at JPGN, Vol. 60, No. 4, page 564, April 2015).
Figure 4A:
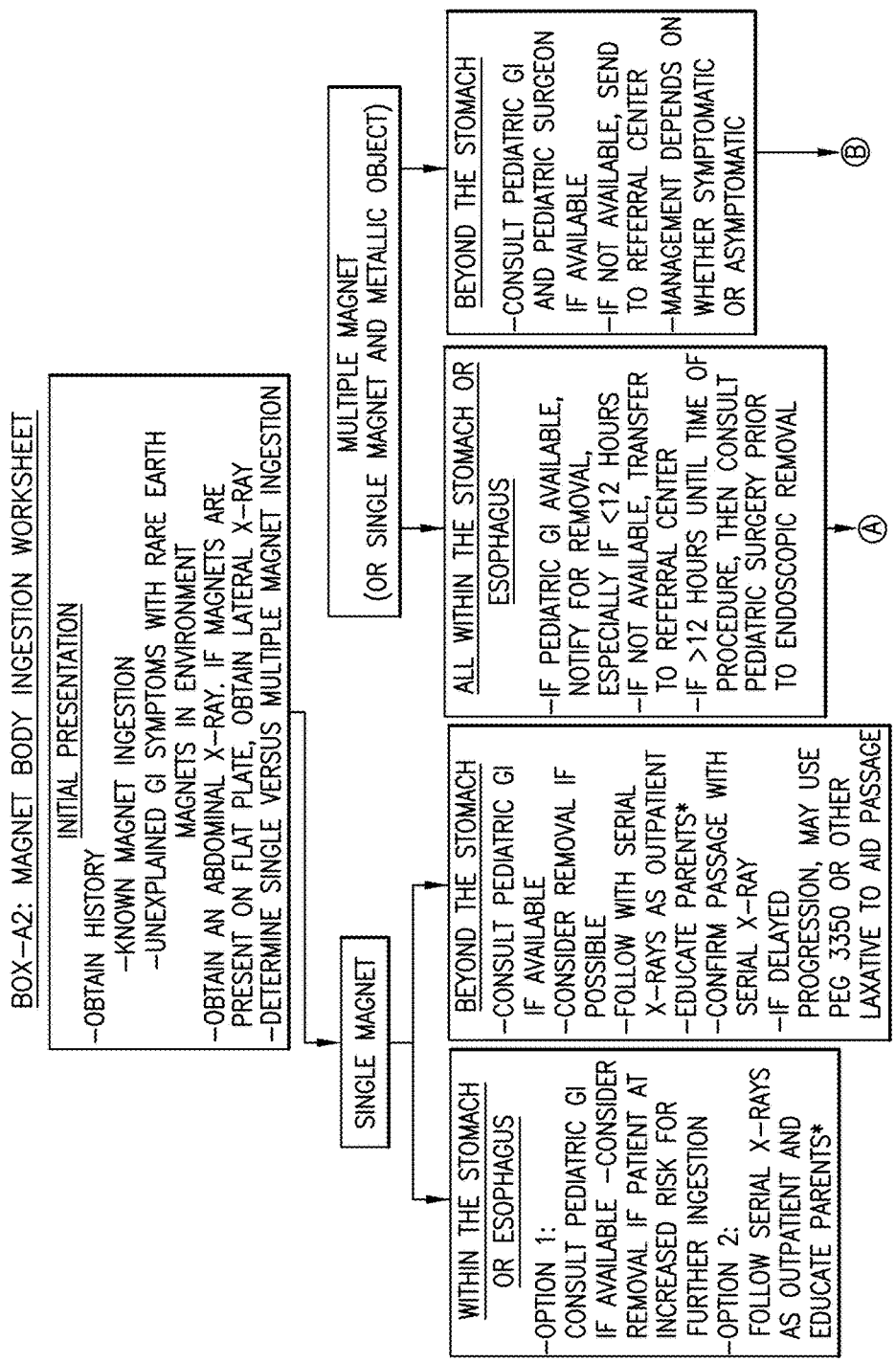
FIG. 4 is a prior art flow chart illustrating a typical magnet ingestion worksheet (available at JPGN, Vol. 60, No. 4, page 567, April 2015).
Figure 4B:
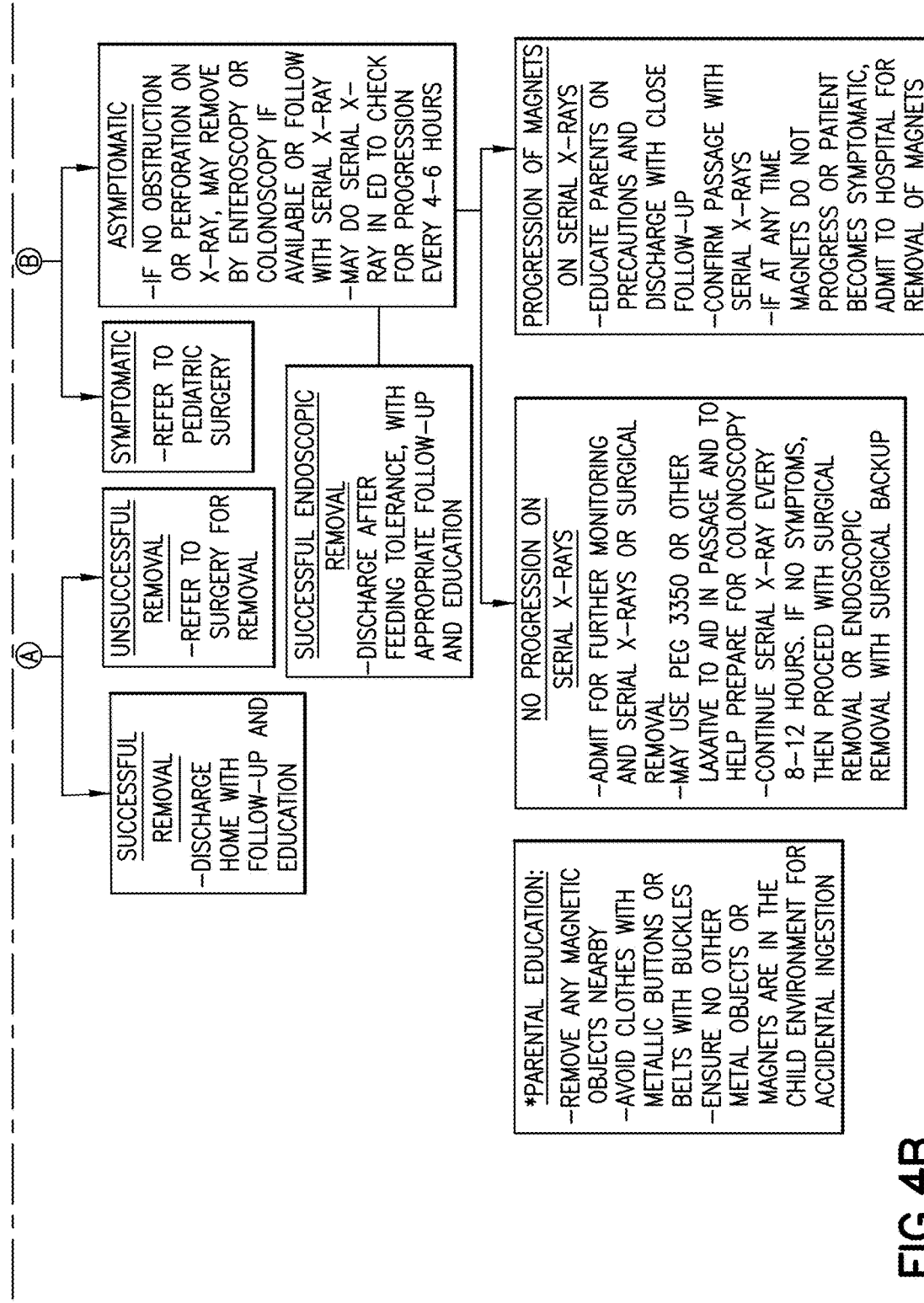
Figure 5:
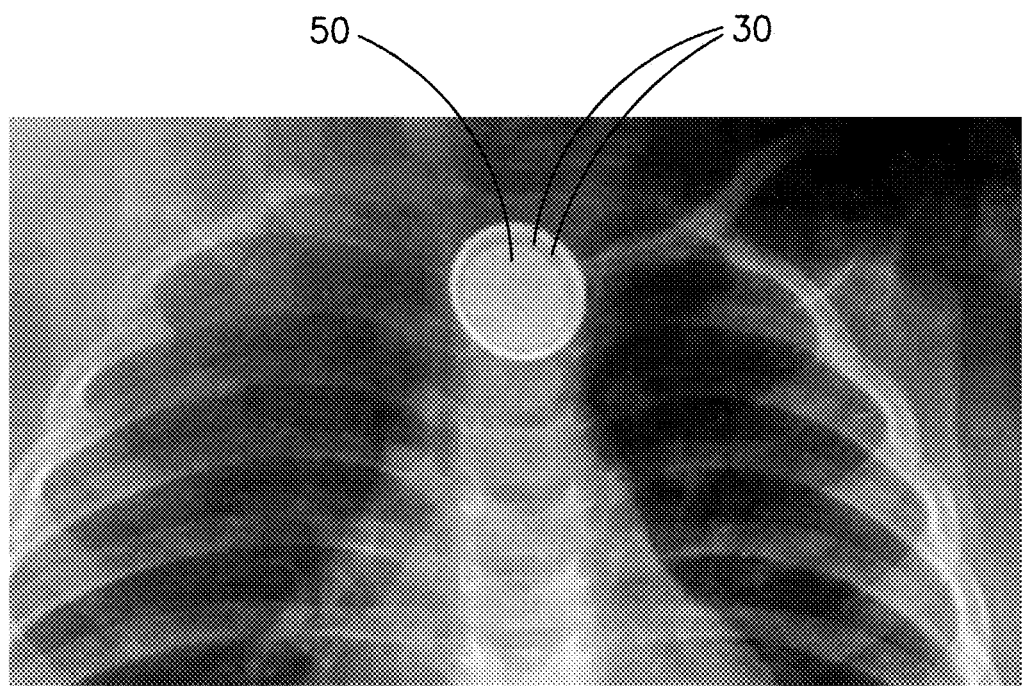
FIG. 5 is a prior art x-ray image (available at http://www.bbc.com/news/health-37410343) illustrating an ingested button battery.

While the present invention is susceptible of embodiment in many different forms, there are shown in the drawings and will be described herein in detail specific exemplary embodiments thereof, with the understanding that the present disclosure is to be considered as an exemplification of the principles of the invention and is not intended to limit the invention to the specific embodiments illustrated. In this respect, before explaining at least one embodiment consistent with the present invention in detail, it is to be understood that the invention is not limited in its application to the details of construction and to the arrangements of components set forth above and below, illustrated in the drawings, or as described in the examples. Methods and apparatuses consistent with the present invention are capable of other embodiments and of being practiced and carried out in various ways. Also, it is to be understood that the phraseology and terminology employed herein, as well as the abstract included below, are for the purposes of description and should not be regarded as limiting.

As mentioned above and as discussed in greater detail below, ingestion of a foreign body can be a life-threating event, with the ingestion of a battery by a small child being an emergency requiring immediate attention. Batteries localized beyond the esophagus rarely need to be retrieved unless the patient manifests signs or symptoms of gastrointestinal tract injury or a large-diameter battery fails to pass beyond the pylorus. Button batteries typically greater than 12 mm in diameter, however, can be trapped in the esophagus with the risk of esophageal burns within 2-2.5 hours and resultant complications. The high degree of morbidity and mortality that has been observed with missed battery ingestions in children has led to renewed focus to determine optimal management of these children. Typically injuries occur if the battery is localized within the esophagus and include tracheoesophageal fistula (47.9%), esophageal perforation in 23.3%, esophageal strictures in 38.4%, vocal cord paralysis from recurrent laryngeal nerve injury in 9.6%. Moreover, mediastinitis, cardiac arrest, pneumothorax, and aortoenteric fistula have been reported (Kramer et al., 2015; Litovitz et al., 2010; Marom et al., 2010). A coin or any other metal object, however, will not do significant damage to the esophagus because of the absence of the electrical current.

Management of battery ingestion includes many steps. It is important to clearly identify the foreign object as a battery and to determine its exact location, for both human and veterinary applications. The representative apparatus 100, 200 and system 300, 400 embodiments measure the magnetic field of the body of the patient or subject, and are able to determine magnetic field variations or disturbances which may be caused by magnets or batteries. Of particular interest are large size button batteries (≥12 mm), which are unlikely pass the esophagus in children. If not removed immediately, they can cause serious damage within 2 to 2.5 hours. In addition, similarly to batteries, ingested magnets constitute an emergency situation as well. Many batteries are made of materials which are toxic. In addition, in the event more than one magnet is ingested, the multiple magnets may clamp around tissue in the GI tract, causing myriad problems such as puncture wounds, other perforations, or impactions, requiring immediate removal of the magnets as well.

Accordingly, it is important to identify batteries and magnets in an early stage of treatment, which can be done with the inventive representative apparatus 100, 200 and system 300, 400 embodiments, described in greater detail below.

Those having skill in the art will recognize that while the representative embodiments are described with reference to a human subject, the representative embodiments are also fully and equally applicable to veterinary applications. For example and without limitation, it would not be uncommon for a dog or cat to ingest a battery or a magnet, and require similarly immediate veterinary attention and treatment.

Representative embodiments provide an apparatus, system and method for early detection and identification of an ingested foreign body as a battery or as a magnet. The representative apparatus embodiments are provided either as one or more hand-held detection apparatuses 100-100H (illustrated in FIGS. 6, 7, and 10) or in form of one or more self-adhesive flexible material layers or "strips" as another type of detection apparatus 200-200D (illustrated in FIGS. 8 and 14-21), all of which include at least one or a plurality of sensitive Hall effect sensors 110 to measure the magnetic field strength over the body (human or other animal), which is or are then used to detect any ingested battery or magnet.

Unless otherwise specified or the context so requires, any reference to a representative battery and magnet detection apparatus 100 or 200 embodiment shall be understood to mean and include, respectively, any and all apparatus 100-100H embodiments or any and all apparatus 200-200D embodiments, respectively. It should also be noted that any reference to measurement of a magnetic field should be understood to mean and include measurement of the magnitude (or strength) of the magnetic field.

Representative battery and magnet detection apparatus 100, 200 and system 300, 400 embodiments measure the magnetic field distribution over the esophagus of the subject, as the location in a subject in which a battery or magnet would become impacted and therefore referred to herein as "target" magnetic field measurements, and compare these target magnetic field measurements with a reference or baseline magnetic field distribution, determined either from calibration of the apparatus 100, 200 or from magnetic field distribution measurements taken a predetermined distance away from the subject's esophagus, such as along the lateral chest and neck of the human body, to avoid interference from a possibly impacted battery or magnet. Representative battery and magnet detection apparatus 100, 200 and system 300, 400 embodiments then determine whether there are statistically significant deviations from reference levels, and if so, selectively identify the foreign body as a battery or a magnet, providing a specific and accurate indication which is not seen with a coin or other ingested non-magnetic metal, and further also determine the approximate location of the ingested battery or magnet. With the representative apparatus 100, 200 and system 300, 400 embodiments, a battery can be detected early and timely management of the patient can reduce battery-related damage, including reducing the likelihood of death of the patient.

The representative apparatus 100, 200 and system 300, 400 embodiments allow medical and other personnel to distinguish between magnetic and non-magnetic ingested foreign bodies. In particular, it will be possible to identify batteries as such at an early stage and guide subsequent treatments. Battery ingestion in children constitutes an emergency with a short time window to remove the battery and avoid serious tissue damage. Because of the possible side effects of an unrecognized battery, it can be important for any ambulance, emergency room, pediatric office, child care center, or home, to be equipped with such a representative apparatus 100, 200 and system 300, 400 embodiment, which can help to streamline the treatment of affected children. Furthermore, the representative apparatus 100, 200 and system 300, 400 embodiments can help concerned parents in the case of foreign body ingestion by one of their children or pets.

Figure 8:
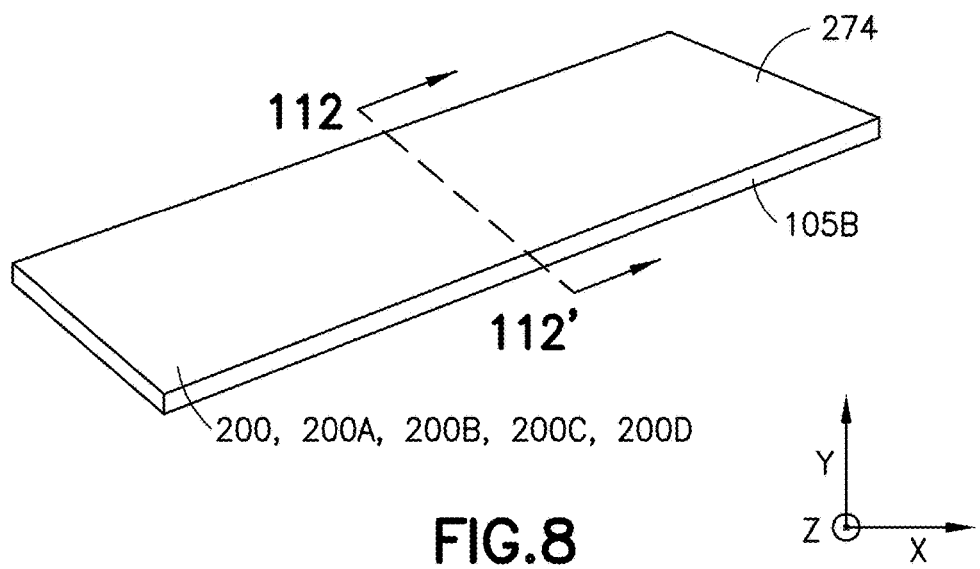
FIG. 8 is an isometric diagram illustrating a third representative battery and magnet detection apparatus embodiment.
Figure 9:
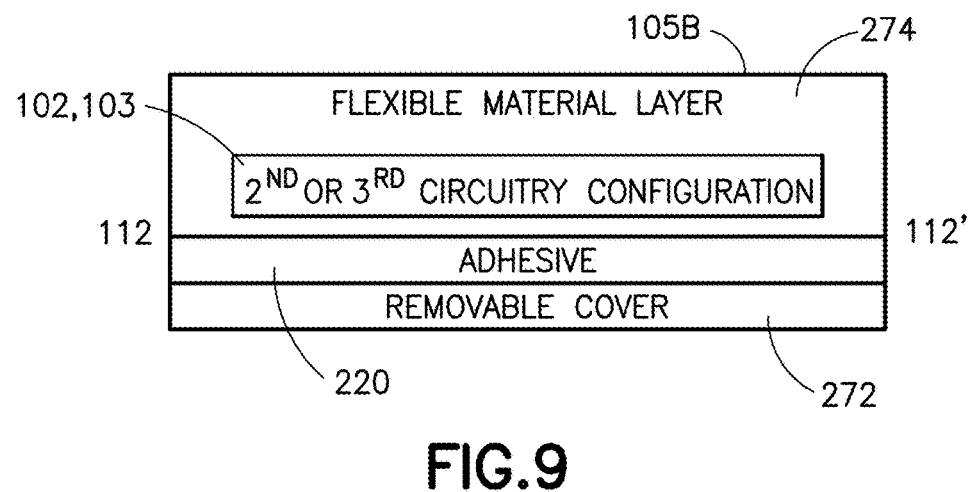
FIG. 9 is cross-sectional diagram (through the 112-112' plane) of the third representative battery and magnet detection apparatus embodiment of FIG. 8.
Figure 10:
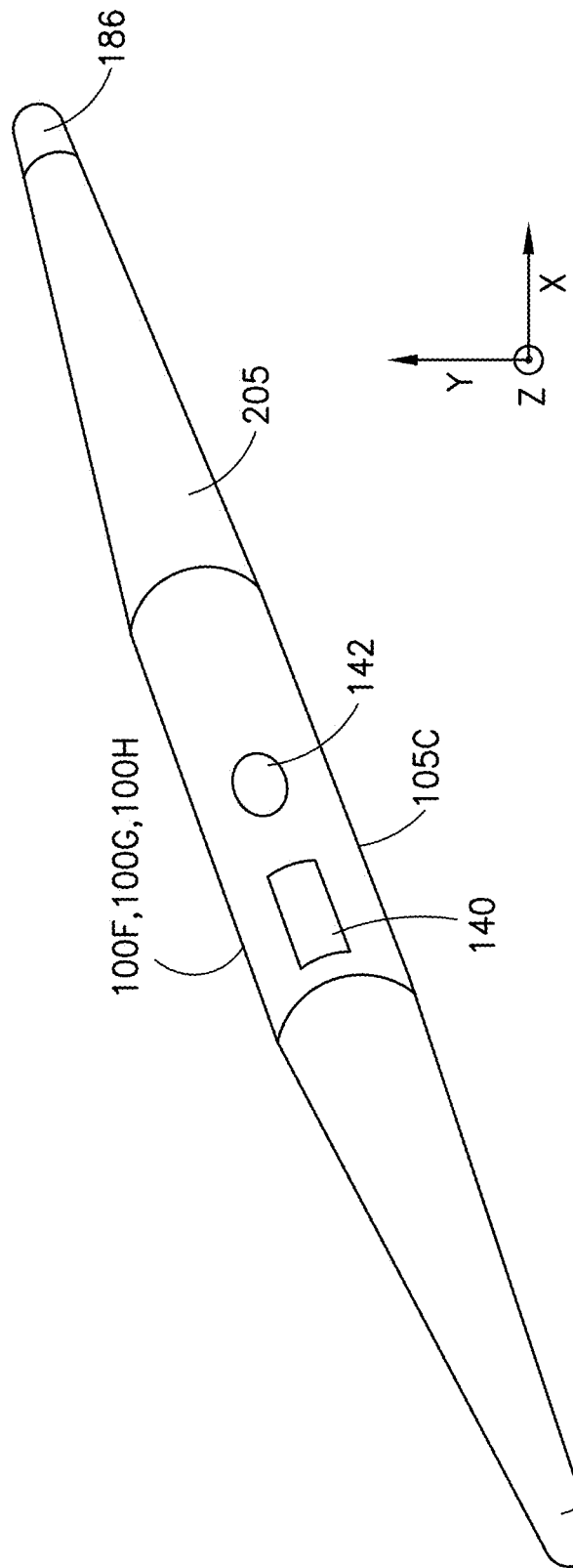
FIG. 10 is an isometric diagram illustrating a fourth representative, hand-held battery and magnet detection apparatus embodiment.

FIG. 6 is an isometric diagram illustrating a first representative, hand-held battery and magnet detection apparatus 100, 100A, 100B embodiment. FIG. 7 is an isometric diagram illustrating a second representative, hand-held battery and magnet detection apparatus 100C, 100D, 100E embodiment. FIG. 8 is an isometric diagram illustrating a third representative battery and magnet detection apparatus 200, 200A, 200B, 200C, 200D embodiment. FIG. 9 is cross-sectional diagram (through the 112-112' plane) of the third representative battery and magnet detection apparatus 200, 200A, 200B, 200C, 200D embodiment of FIG. 8. FIG. 10 is an isometric diagram illustrating a fourth representative, hand-held battery and magnet detection apparatus 100F, 100G, 100H embodiment.

Figure 11:
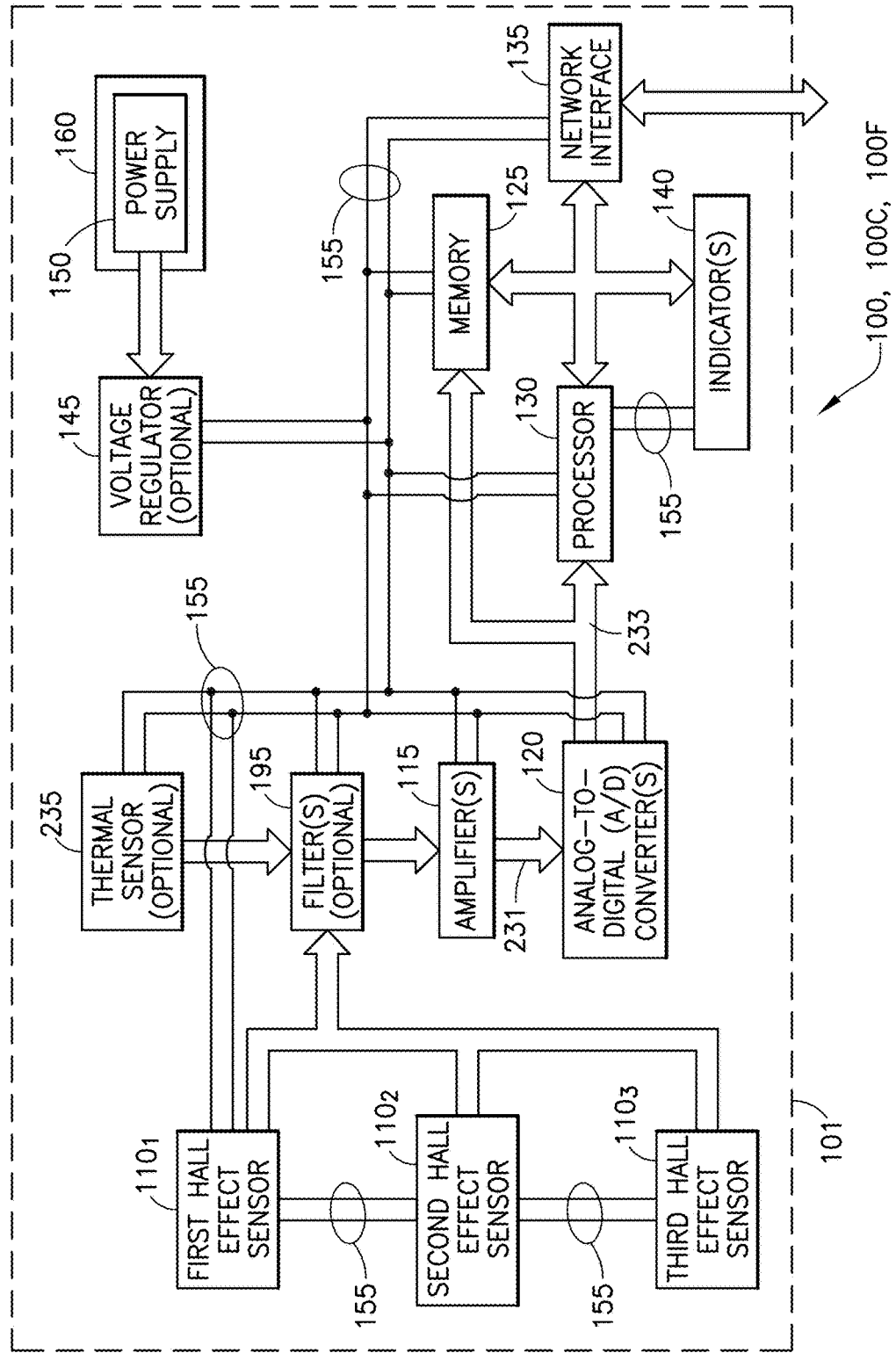
FIG. 11 is a block diagram illustrating a first circuitry configuration for the first, second and fourth representative battery and magnet detection apparatus embodiments.
Figure 12:
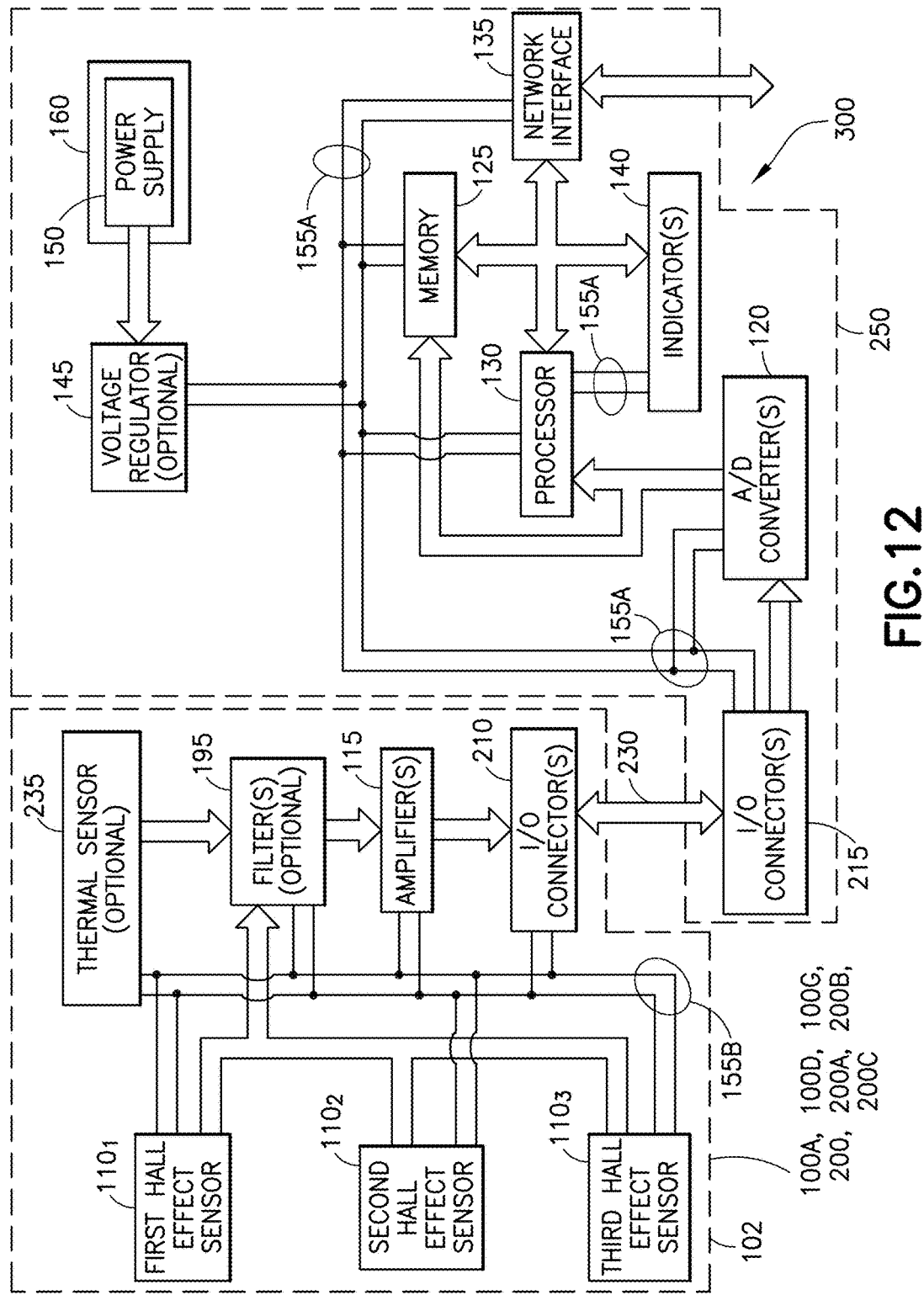
FIG. 12 is a block diagram illustrating a second circuitry configuration for the first, second, third and fourth representative battery and magnet detection apparatus embodiments, a first monitor embodiment, and a first representative battery and magnet detection system embodiment.
Figure 13:
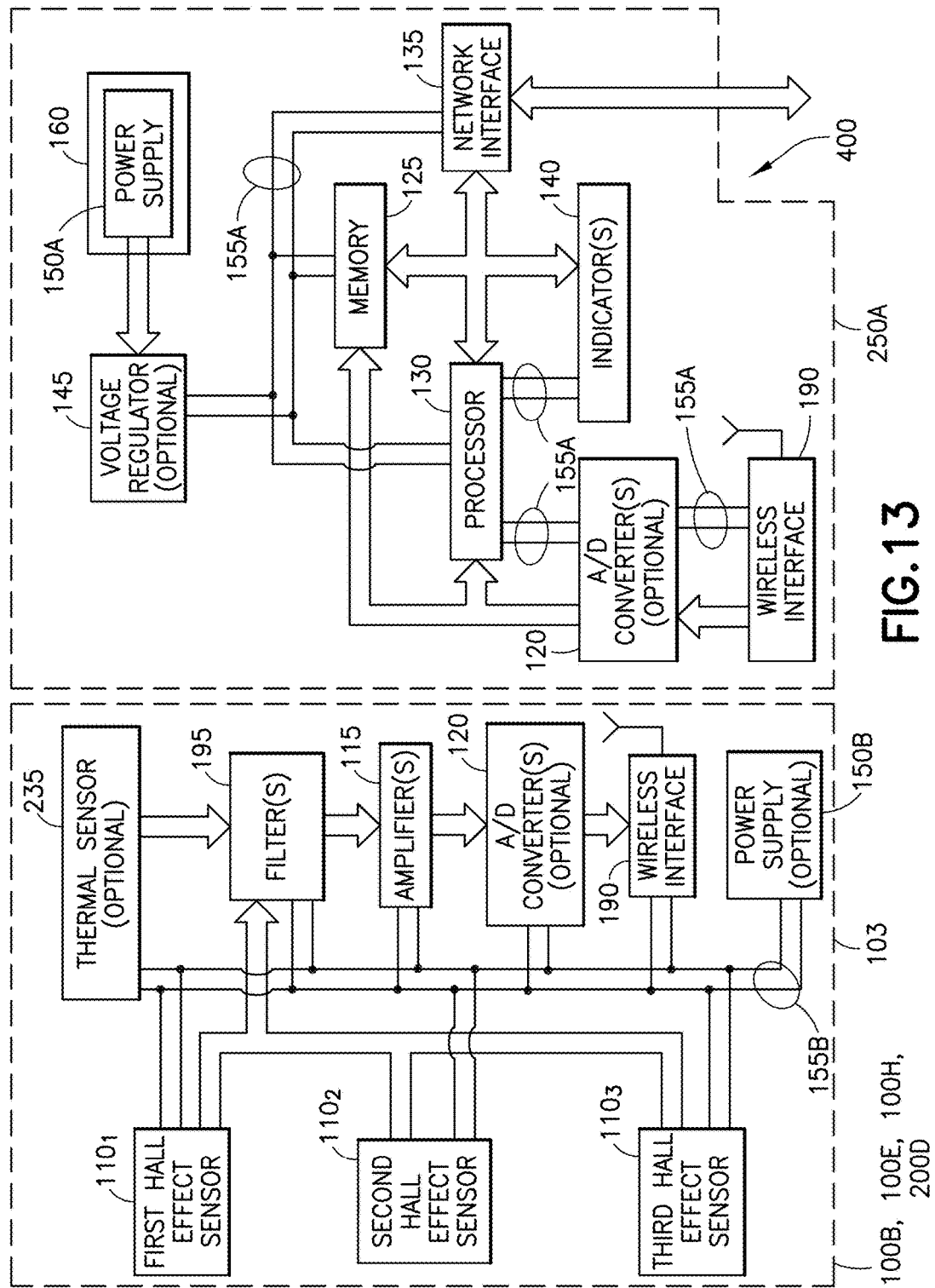
FIG. 13 is a block diagram illustrating a third circuitry configuration for the first, second, third, and fourth representative battery and magnet detection apparatus embodiments, a second monitor embodiment, and a second representative battery and magnet detection system embodiment.
Figure 14:
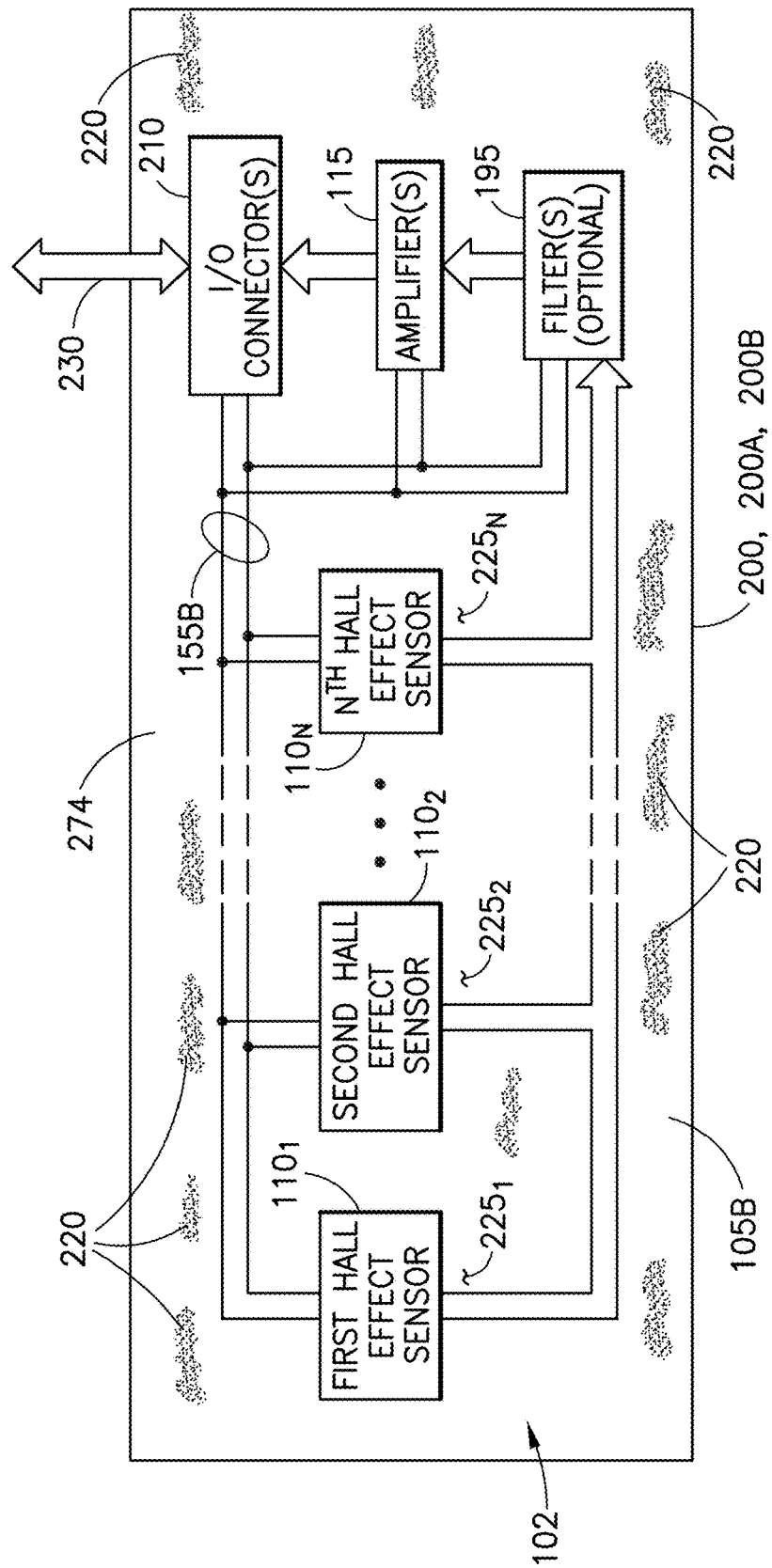
FIG. 14 is a first circuit and block diagram illustrating the second circuitry configuration for the third representative battery and magnet detection apparatus embodiment.
Figure 15:
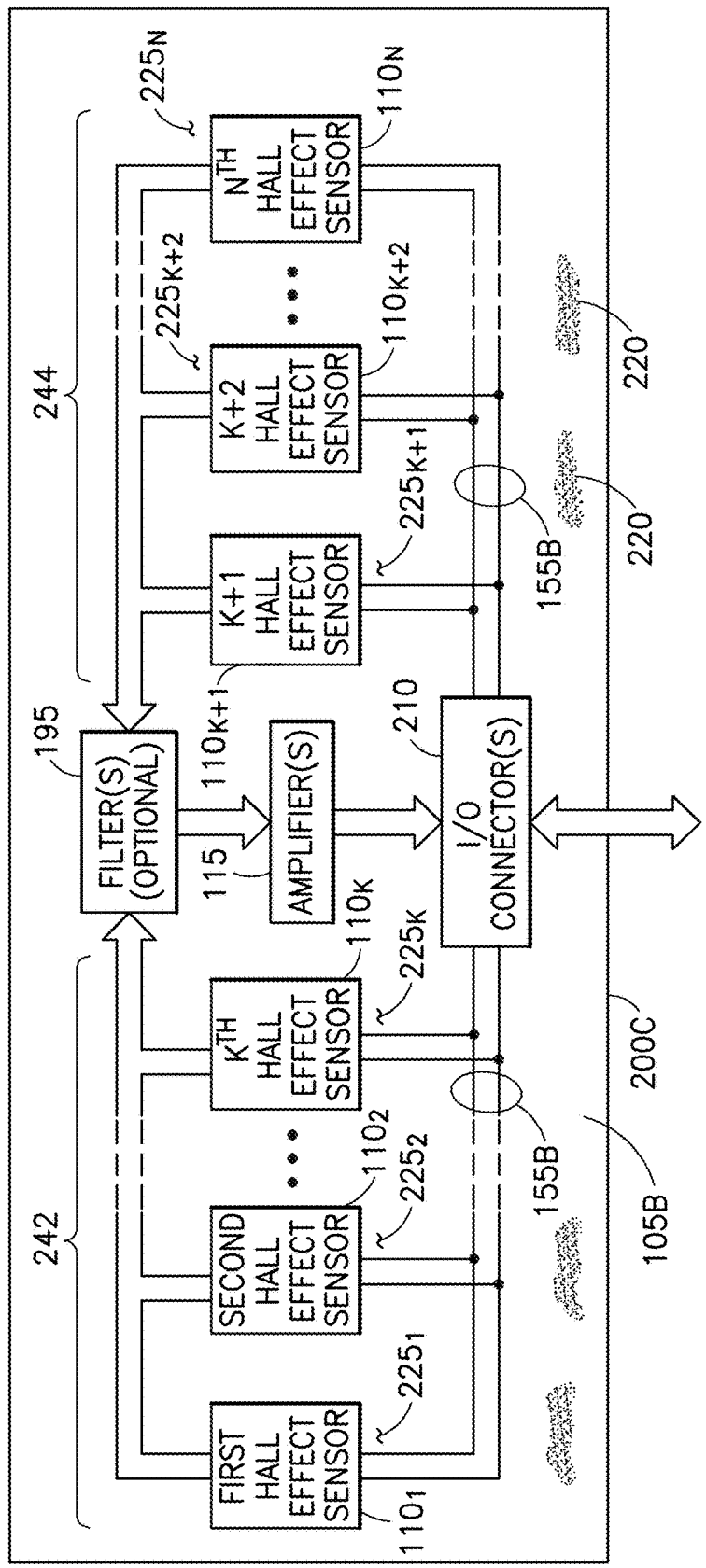
FIG. 15 is a second circuit and block diagram illustrating the second circuitry configuration for the third representative battery and magnet detection apparatus embodiment.
Figure 16:
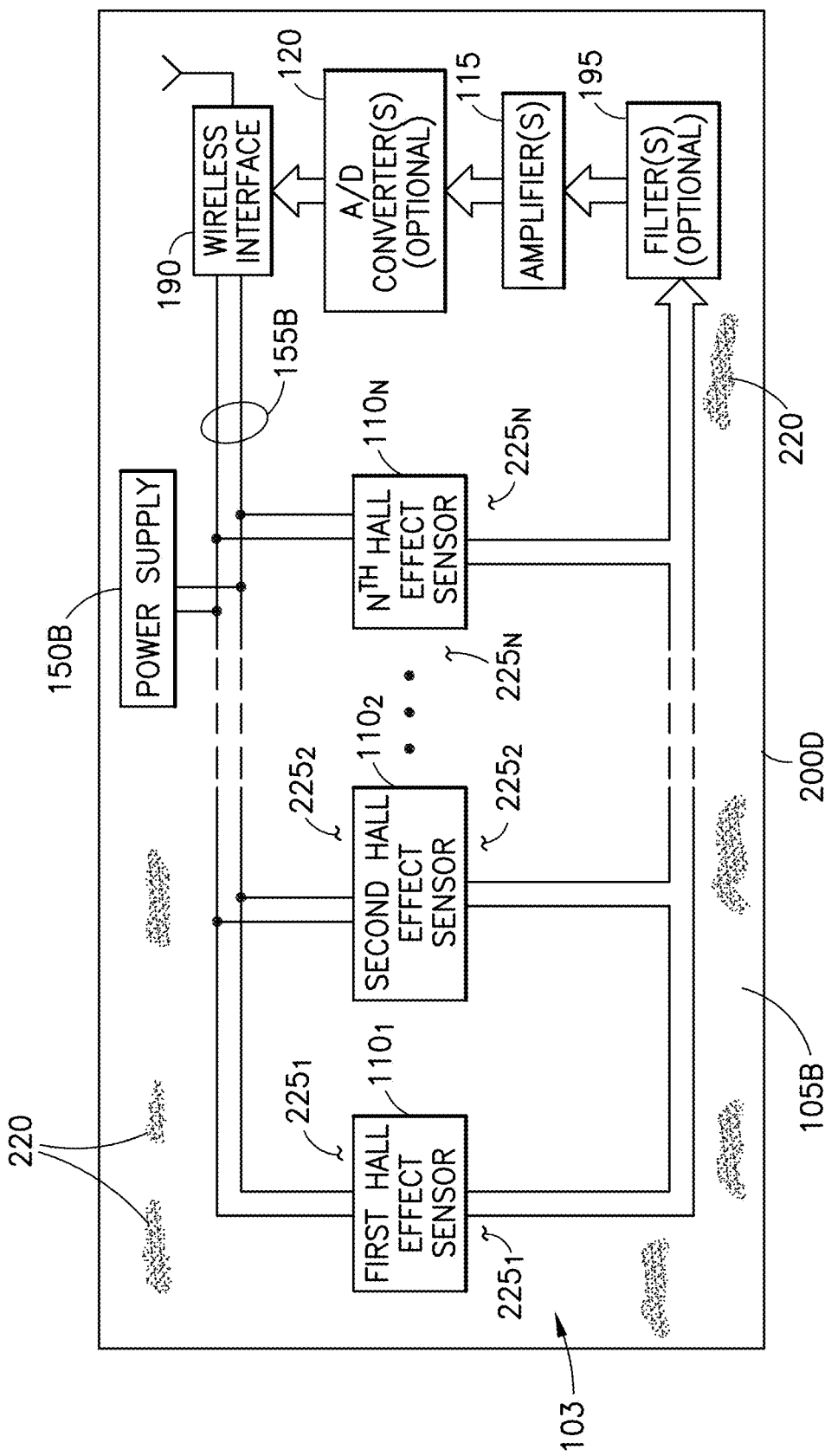
FIG. 16 is a third circuit and block diagram illustrating the third circuitry configuration for the third representative battery and magnet detection apparatus embodiment.
Figure 17:
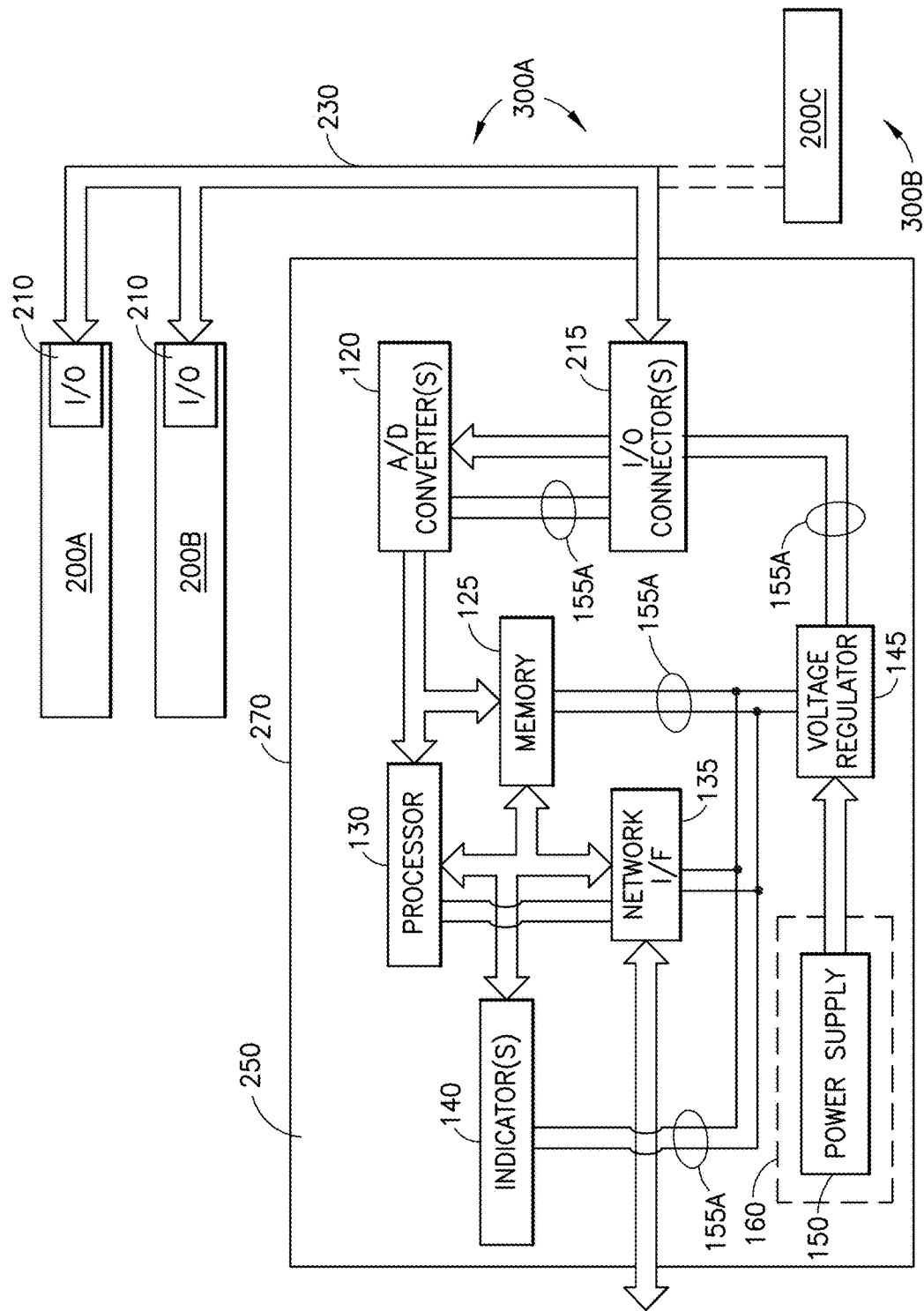
FIG. 17 is a block diagram illustrating the third representative battery and magnet detection apparatus embodiments used in the first representative battery and magnet detection system embodiment.
Figure 18:
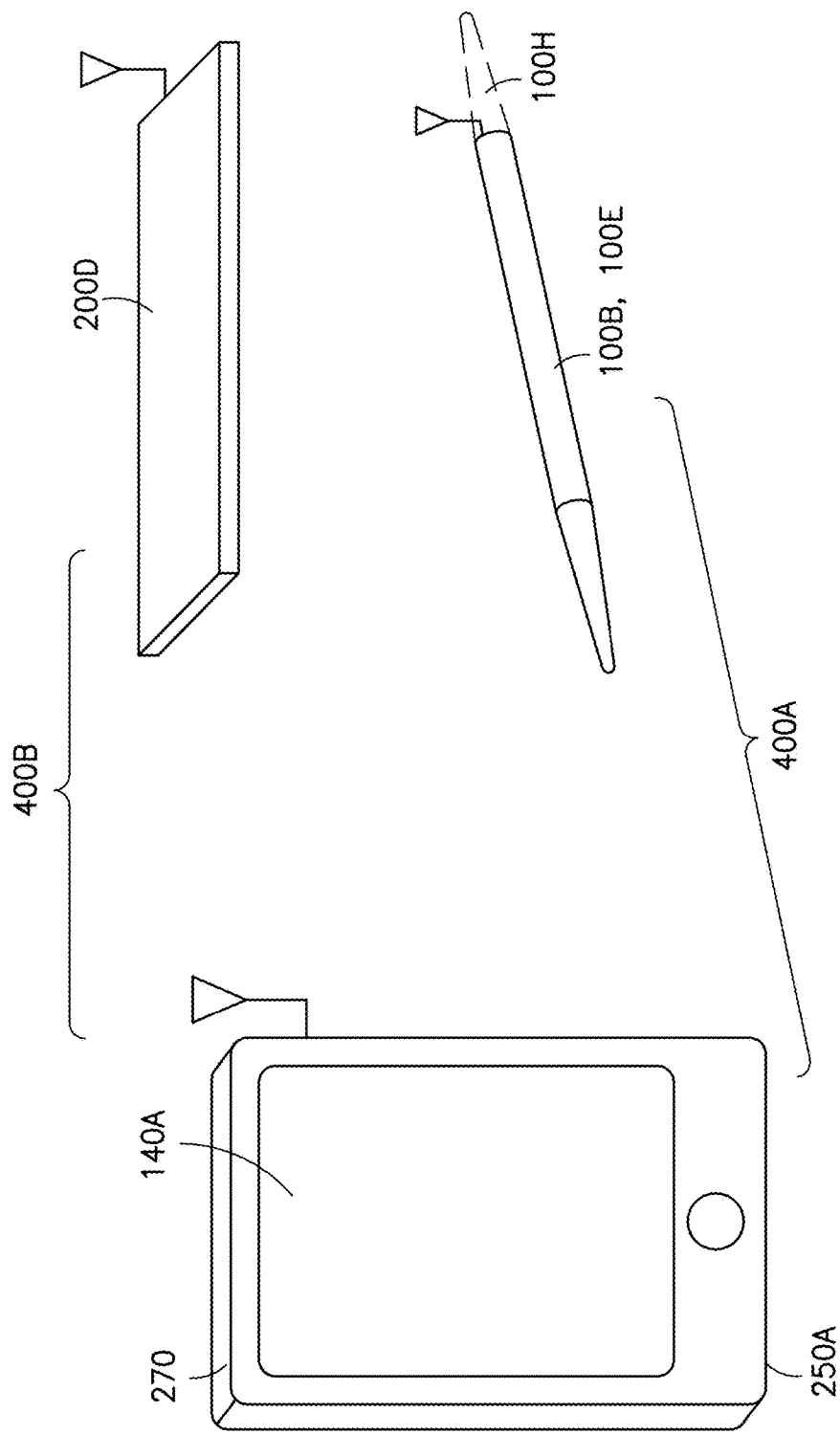
FIG. 18 is a block diagram illustrating the third representative battery and magnet detection apparatus embodiments used in the second representative battery and magnet detection system embodiment.
Figure 19:
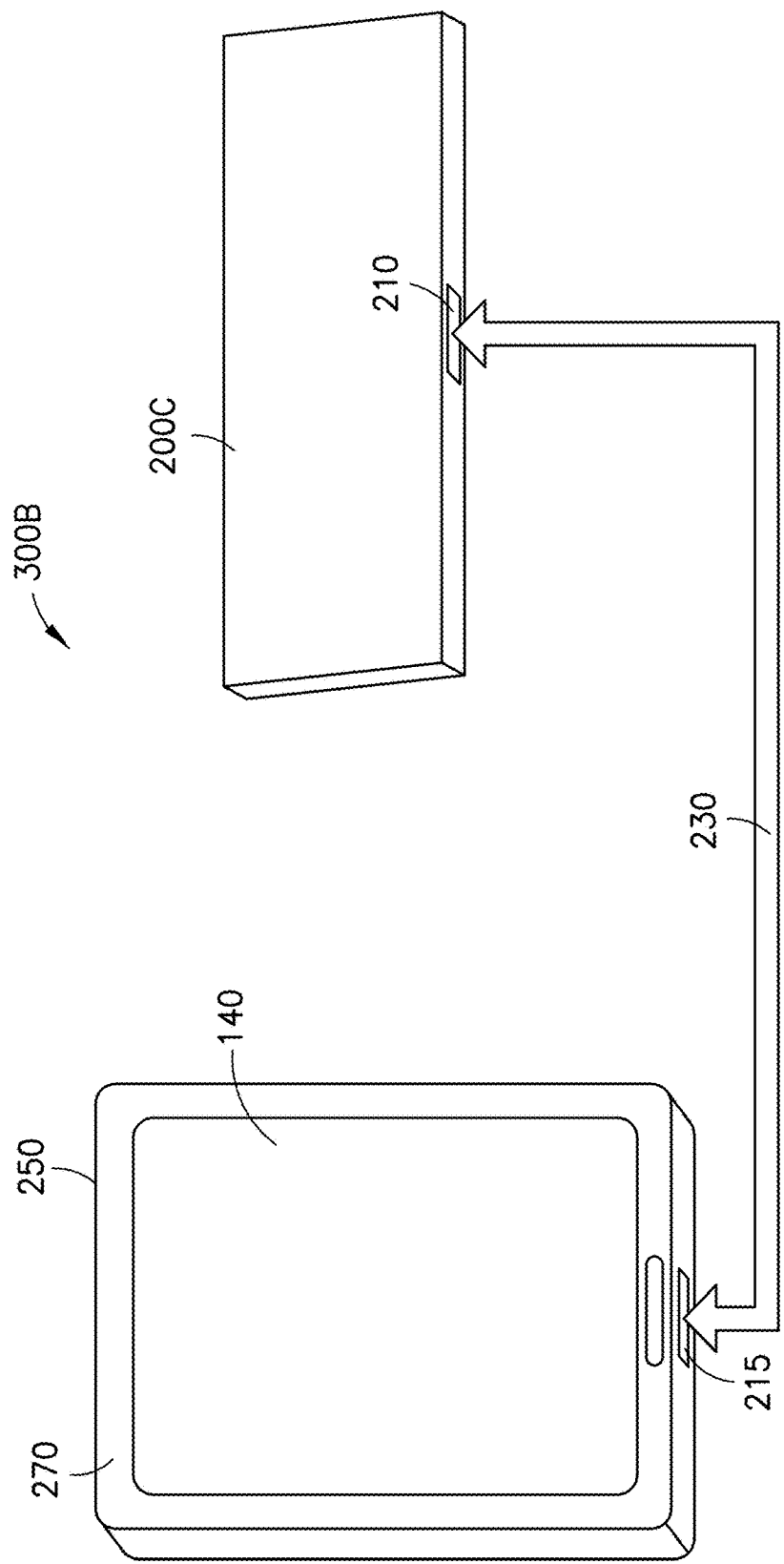
FIG. 19 is a block diagram illustrating the third representative battery and magnet detection apparatus embodiments used in the first representative battery and magnet detection system embodiment.
Figure 20:
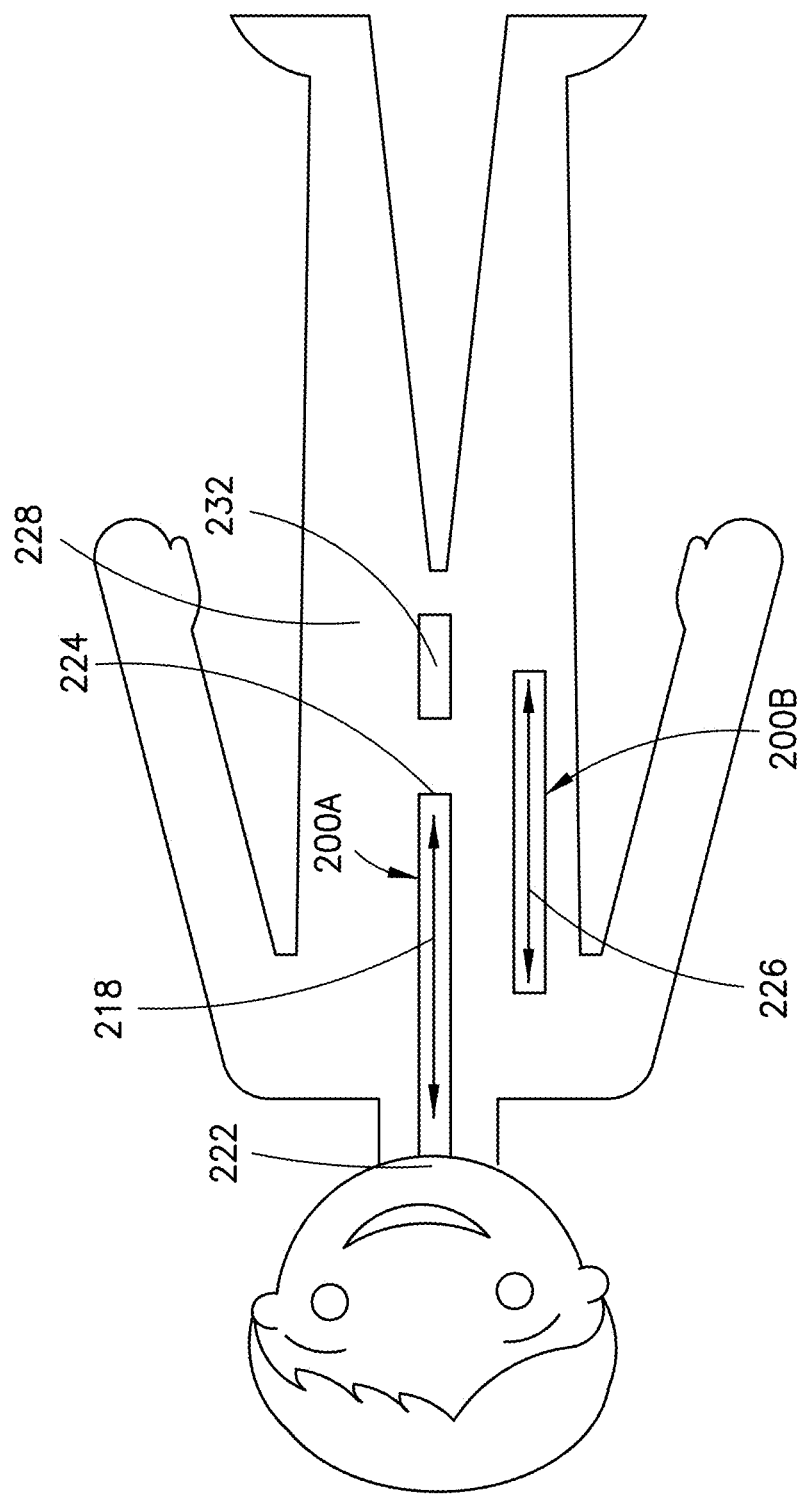
FIG. 20 is a plan view diagram illustrating a first representative placement of third representative battery and magnet detection apparatus embodiments on a human subject.
Figure 21:
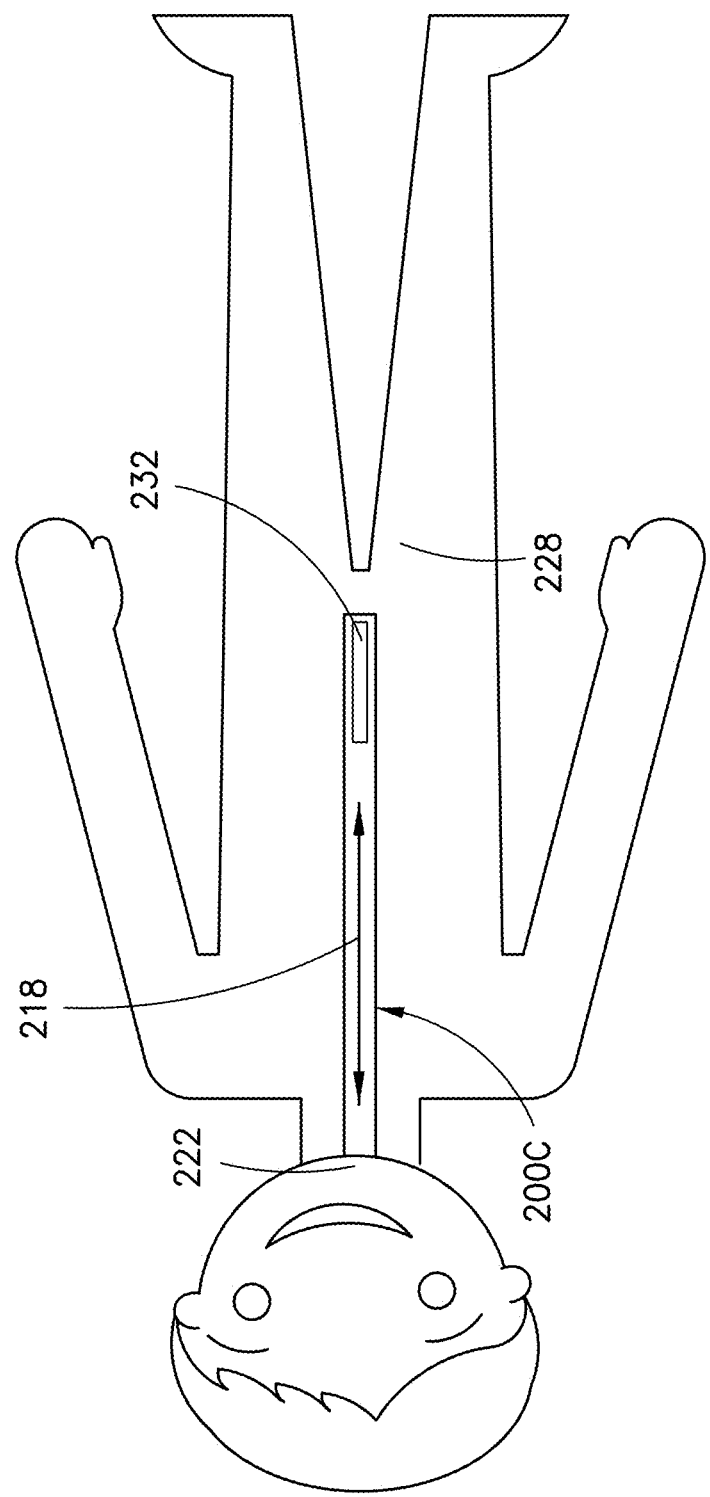
FIG. 21 is a plan view diagram illustrating a second representative placement of the third representative battery and magnet detection apparatus embodiments on a human subject.

FIG. 11 is a block diagram illustrating a first circuitry configuration 101 for the first, second, and fourth representative battery and magnet detection apparatus 100, 100C, 100F embodiments. FIG. 12 is a block diagram illustrating a second circuitry configuration 102 for the first, second, third, and fourth representative battery and magnet detection apparatus 100A, 100D, 100G, 200A, 200B, 200C embodiments, a first monitor 250 embodiment, and a first representative battery and magnet detection system 300 embodiment. FIG. 13 is a block diagram illustrating a third circuitry configuration 103 for the first, second, third, and fourth representative battery and magnet detection apparatus 100B, 100E, 100H, 200D embodiments, a second monitor 250A embodiment, and a second representative battery and magnet detection system 400 embodiment. FIG. 14 is a first circuit and block diagram illustrating the second circuitry configuration 102 for the third representative battery and magnet detection apparatus 200A, 200B embodiments. FIG. 15 is a second circuit and block diagram illustrating the second circuitry configuration 102 for the third representative battery and magnet detection apparatus 200C embodiment. FIG. 16 is a third circuit and block diagram illustrating the third circuitry configuration 103 for the third representative battery and magnet detection apparatus 200D embodiment. FIG. 17 is a block diagram illustrating the third representative battery and magnet detection apparatus embodiments 200A, 200B, 200C used in the first representative battery and magnet detection system 300 embodiment. FIG. 18 is a block diagram illustrating the third representative battery and magnet detection apparatus 200D embodiments used in the second representative battery and magnet detection system 400 embodiment. FIG. 19 is a block diagram illustrating the third representative battery and magnet detection apparatus embodiment 200C used in the first representative battery and magnet detection system embodiment. FIG. 20 is a plan view diagram illustrating a first representative placement of third representative battery and magnet detection apparatus 200A, 200B, 200D embodiments on a human subject. FIG. 21 is a plan view diagram illustrating a second representative placement of the third representative battery and magnet detection apparatus 200C embodiments on a human subject.

Figure 22:
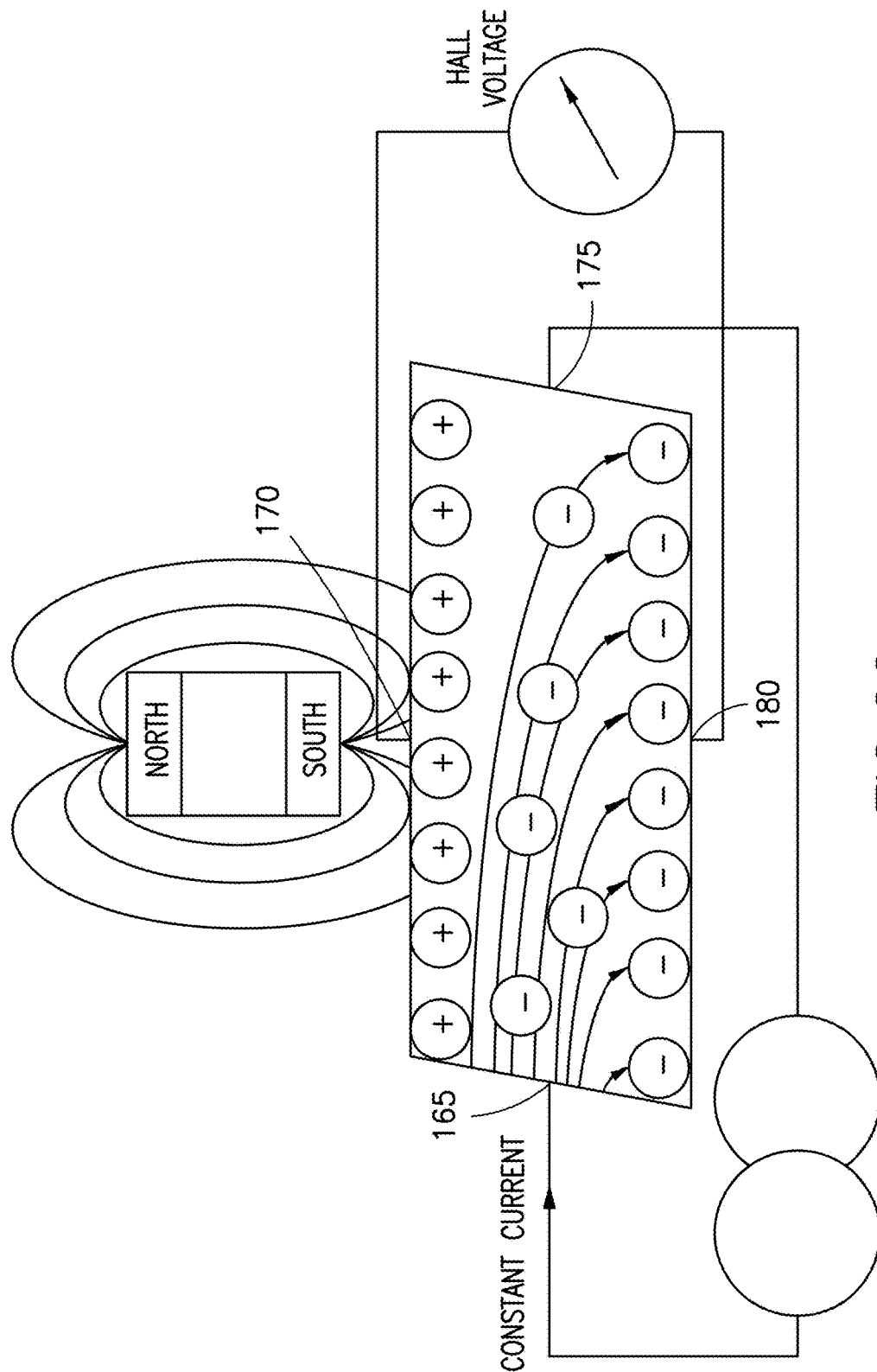
FIG. 22 is a block diagram illustrating generation of a Hall effect voltage.
Figure 23:
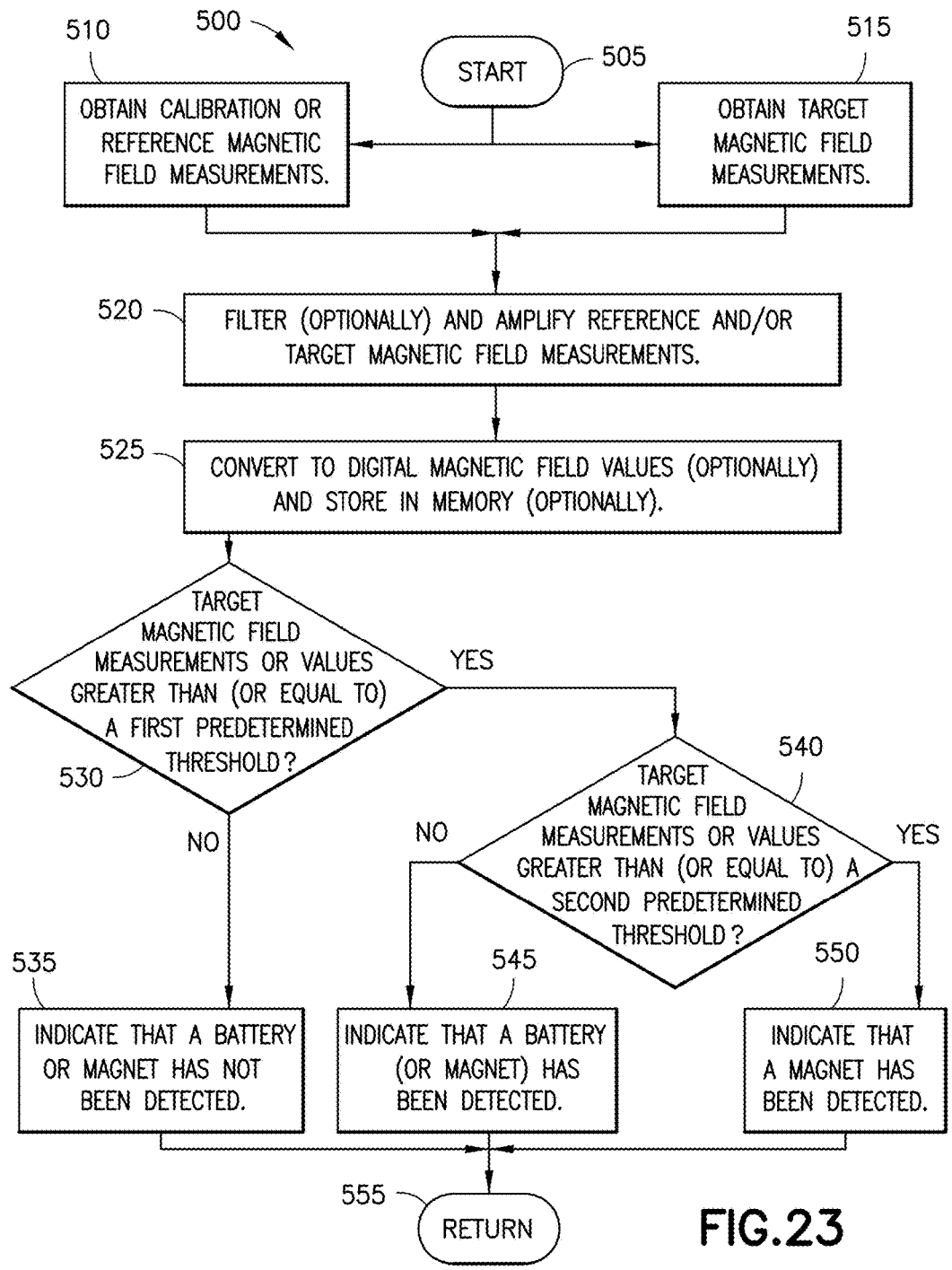
FIG. 23 is a flow chart diagram illustrating a first representative method embodiment.
Figure 24:
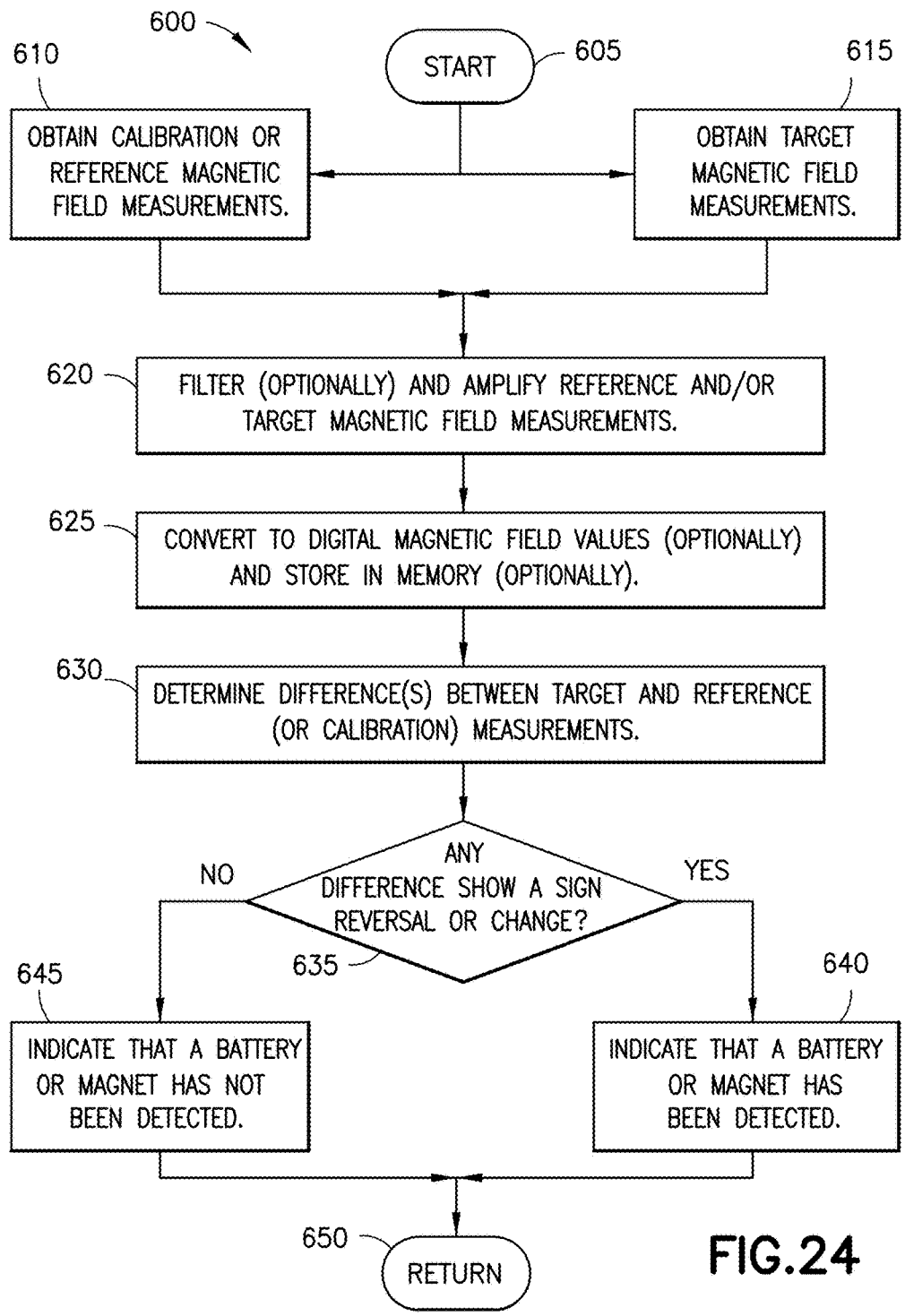
FIG. 24 is a flow chart diagram illustrating a second representative method embodiment.
Figure 25:
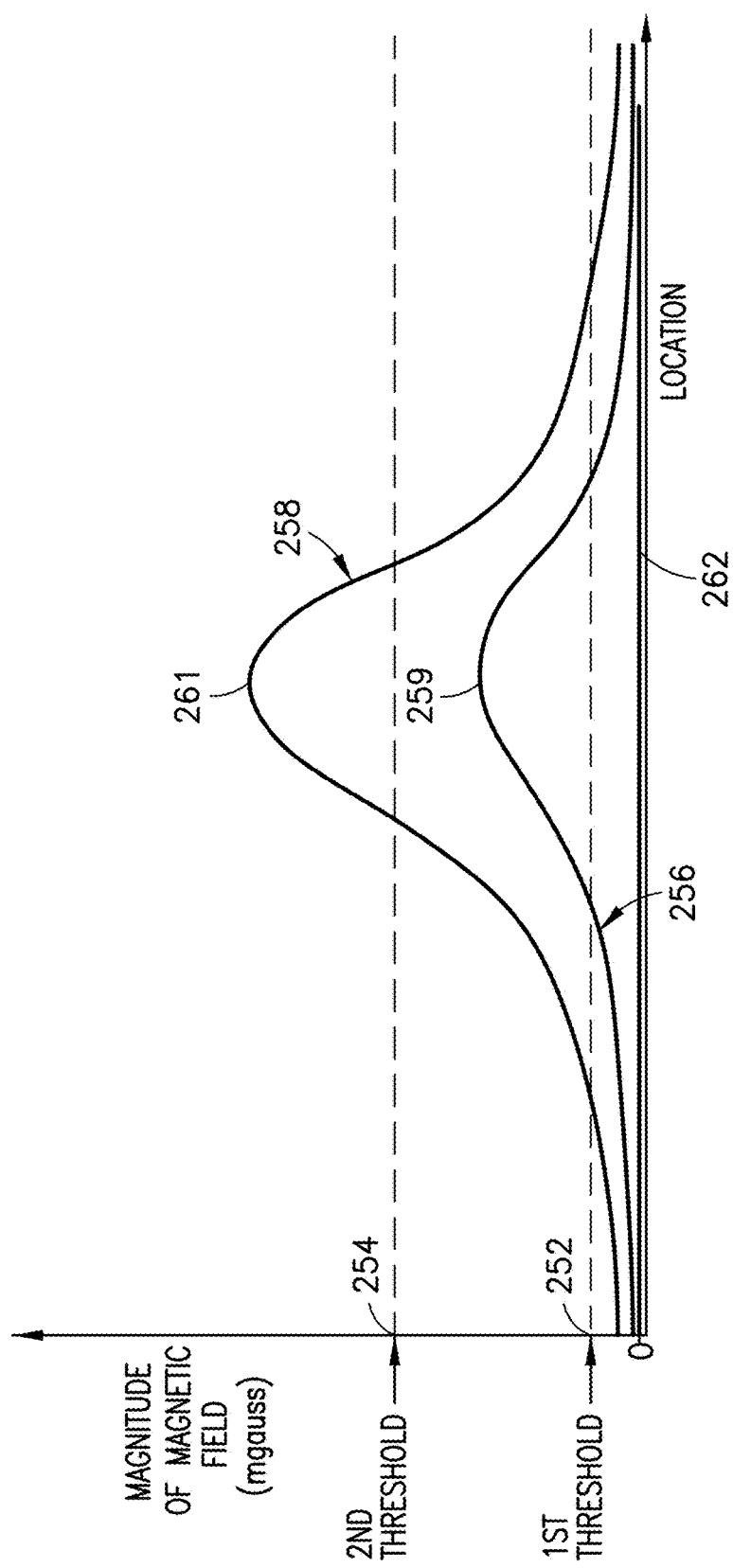
FIG. 25 is a graphical diagram illustrating exemplary or representative magnetic field measurements for detection of a battery or a magnet.

FIG. 22 is a block diagram illustrating generation of a Hall effect voltage. FIG. 23 is a flow chart diagram illustrating a first representative method 500 embodiment. FIG. 24 is a flow chart diagram illustrating a second representative method 600 embodiment. FIG. 25 is a graphical diagram illustrating exemplary or representative magnetic field measurements for detection of a battery or a magnet. FIG. 26 is a graphical diagram illustrating magnetic field measurements taken from three human cadavers after a battery or a coin (as a reference object) was inserted in the esophagus. FIG. 27 is a bar chart illustrating magnetic field measurements taken from three human cadavers after a battery or a coin (as a reference object) was inserted in the esophagus.

Referring to FIGS. 6-21, representative apparatus 100-100H, 200-200D and system 300, 400 embodiments use one or more sensitive Hall effect sensors 110 to measure the magnitude or strength of the magnetic field of the body. The various representative apparatus 100-100H, 200-200D and system 300, 400 embodiments differ from one another insofar as:

(1) having different form factors and types of housings 105, 105A, 105B, 105C;
(2) having wireless or wired communication between an apparatus 100A, 100B, 100D, 100E, 100G, 100H, 200 - 200D and monitor 250, 250A in a system 300, 400;
(3) in the electronic components being either (a) completely and entirely self-contained in a single apparatus 100, 100C, 100F or (b) distributed between and among the apparatus 100A, 100B, 100D, 100E, 100G, 100H, 200-200D embodiments and respective monitor 250, 250A embodiments (collectively forming corresponding system 300, 400 embodiments), and in this latter case, having added communication functionality for communication between the apparatus 100A, 100B, 100D, 100E, 100G, 100H, 200-200D embodiments and monitor 250, 250A embodiments; and
(4) the inclusion of additional sensors, such as optional thermal sensors 235, in the apparatus 100F, 100G, 100H embodiments.

First, the representative apparatus 100-100H, 200-200D, monitor 250, 250A, and system 300, 400 embodiment may have any suitable form factors and housings, and those which are illustrated are merely examples, with many other possible form factors available, and with any and all of which considered equivalent and within the scope of the disclosure. The first, second and fourth representative battery and magnet detection apparatus 100-100H embodiments are illustrated as having a representative hand-held form factor, such as a generally cylindrical "wand" apparatus 100, 100A, 100B, 100F, 100G, 100H, or a generally disc-shaped apparatus 100C, 100D, 100E, and other than the distribution of electronic components mentioned above, differ only with respect to the shape of the housing 105, 105A, 105C, locations of the (optional) indicator 140 and power on/off button or switch 142, and potential location of the one or more Hall effect sensors 110 within the housing 105, 105A, 105C, and are generally designed for repeated use among many patients. The third representative battery and magnet detection apparatus 200-200D embodiments have a form factor of a flexible material layer or strip (forming a housing 105B) with an adhesive and with a generally linear array of Hall effect sensors 110, and are generally designed for single use per patient. The apparatus 100A, 100D, 100G, 200A, 200B, and 200C embodiments have wired communication with the monitor 250, forming a corresponding system 300 embodiment, while the apparatus 100E, 100H, and 200D embodiments have wireless communication with the monitor 250A, forming a corresponding system 400 embodiment. The various monitor 250, 250A embodiments also may have any suitable form factors and corresponding housings 270, configured such as stand-alone computers, laptops, docking stations, smartphones, other hand-held devices, etc. Those having skill in the electronic arts will recognize that innumerable variations are available, any and all of which are considered equivalent and within the scope of the disclosure.

Second, with regard to the distribution of the electronic components between and among the various apparatus 100-100H, 200-200D and monitor 250, 250A embodiments, for the apparatus 100, 100C, 100F embodiments, all of the electronic components are entirely self-contained in the housing 105, 105A, 105C, respectively, with these apparatus 100, 100C, 100F embodiments illustrated as having the first circuitry configuration 101 (FIG. 11). For these embodiments, no separate monitor 250 or system 300, 400 is utilized or otherwise required. The apparatus 100A, 100D, 100G, 200A, 200B, and 200C embodiments utilize the second circuitry configuration 102 (FIG. 12) with wired communication to the monitor 250, forming a corresponding system 300 embodiment. The apparatus 100E, 100H, and 200D embodiments utilize the third circuitry configuration 103 (FIG. 13) with wireless communication to the monitor 250A, forming a corresponding system 400 embodiment. The apparatus 100F, 100G, and 100H embodiments utilize the first, second or third circuitry configurations 101, 102, 103, respectively, and further include at least one optional additional sensor, such as an optional thermal sensor 235, effectively forming a combination apparatus having at least two devices in combination, such as both a battery or magnet detector and a thermometer 205. Those having skill in the electronic arts will recognize that innumerable variations are available, any and all of which are considered equivalent and within the scope of the disclosure.

Referring to FIG. 22, an electric current is typically carried by the displacement of electrons. In the absence of a magnetic field, when an electric current flows through a conducting material, electrons move in a generally linear fashion between the first and second electrical contacts 165, 175 (illustrated from left to right in FIG. 22), and the voltage difference between the third, top contact 170 and the fourth, bottom contact 180 is about zero. In case the conducting material is placed in a magnetic field, the Lorentz force is then acting on the electrons, and this presence of the magnetic field results in the deviation of the electrons from their generally straight path and generates a measurable voltage difference between the third, top contact 170 and the fourth, bottom contact 180. This voltage is proportional to the magnitude or strength of the magnetic field and is referred to herein as the Hall effect voltage or Hall effect voltage signal, and is used advantageously in the representative embodiments to measure the strength of magnetic fields provided or generated by batteries or magnets.

Referring to FIGS. 6-27, for the first, second, and fourth representative battery and magnet detection apparatus 100-100H embodiments, one of the hand-held, generally cylindrical "wand" apparatus 100, 100A, 100B, 100F, 100G, 100H or disc-shaped apparatus 100C, 100D, 100E, each having one or more Hall effect sensors 110, is moved along (and typically touching or just hovering above) the subject's body following a predetermined line as a "trace", and generally consistently during and among traces, such as generally at a predetermined and/or consistent speed, and with a consistent orientation of the apparatus 100-100H. For example and without limitation, the one or more Hall effect sensors 110 may be arranged in the tip 185 of the apparatus 100, 100A, 100B, 100F, 100G, 100H, or in the center 187 or a designated location of the apparatus 100C, 100D, 100E, which is or are then moved along the subject body at one or more designated locations. While moving the apparatus 100-100H, the magnitude of the magnetic field of the body is measured continuously or at discrete intervals (e.g., at a sufficiently high frequency to generate a sufficient number of values for comparison, such as a sampling rate of 1-10 kHz, for example and without limitation), and depending on the calibration (if any), over at least one or two different regions of the subject's body 228 (FIGS. 20 and 21), and the values for the target magnetic field magnitude (or strength) or reference (or calibrated magnetic field magnitude (or strength)) can be plotted versus location and stored in a memory 125 (or cache or memory of a processor 130), or more simply compared to the reference or calibration values.

Referring to FIG. 20, a first trace, as a series of target magnetic field measurements, is performed by moving the apparatus 100-100H on the subject's body 228 over a first region or location 218 (indicated with an arrow), which is generally over (anterior to) the esophagus of the subject, such as moving the apparatus 100-100H from the tip of the subject's chin 222 and extending to the distal end of the sternum, generally around the xiphoid process 224, with measurements in the presence of a battery or magnet illustrated respectively as lines 256, 258 in FIG. 25 and as lines 266, 268 (battery only) in FIG. 26. Referring to FIG. 25, it should be noted that in the event multiple batteries or magnets have been ingested, multiple peaks or maxima may be present, not merely the illustrated single peaks (maxima 259, 261).

In either a first method 500 or a second method 600, step 510 or 610, the apparatus 100-100H may have been calibrated in advance of the first trace. For example, when an apparatus 100-100H is initially turned on (power button or switch 142), it is positioned or otherwise held at a "calibration" location which is spaced-apart a sufficient distance from the location of the potentially impacted battery or magnet (which, if present, would be located in or near the first region or location 218) to detect and measure the ambient magnetic field magnitude or strength, without any significant interference or influence of any magnetic field from the potentially impacted battery or magnet in or near the first region or location 218. Once the apparatus 100-100H is initially turned on and positioned at a calibration location, under the control of a processor 130, the apparatus 100-100H performs a series of measurements of the magnitude or strength of the magnetic field (e.g., for a predetermined period of time or a predetermined number of measurements following powering on or "booting up" of the apparatus 100-100H), thereby providing one or more calibration, reference or baseline magnetic field magnitude (or strength) measurements, illustrated as line 262 in FIG. 25, e.g., "zeroing" the apparatus 100-100H at the measured magnitude or strength of the ambient magnetic field.

In either a first method 500 or a second method 600, step 510 or 610, when the apparatus 100-100H has not been calibrated in advance, a second trace is performed to provide a series of reference or baseline measurements. The second trace is performed by moving the apparatus 100-100H over a second region or location 226 (also indicated with an arrow) of the subject's body 228 (FIG. 20), which is spaced-apart a predetermined distance from the first region or location 218, such as generally spaced-apart laterally and parallel to the first trace (over the first region 218), such as moving the apparatus 100-100H along one side of the subject's chest, illustrated as region 226 in FIG. 20, or superior to the chin 222, or spaced-apart inferiorly to the first region or location 218, such as region 232. It should be noted that the first and second traces may be performed in either order, and in either direction (cranial-caudal or caudal-cranial, for example), and may also be repeated one or more times as may be necessary or advisable.

In the first method 500, determining whether the magnitude or variance of the target magnetic field magnitude (or strength) measurements is greater than a first (252) predetermined threshold (step 530) or a second (254) predetermined threshold (step 540) allows the identification of a battery or magnet, respectively. The first (252) and second (254) predetermined threshold levels are typically determined empirically and set at respective levels above or greater than the reference or calibrated magnetic field magnitude (or strength). The first (252) and second (254) predetermined threshold levels may be included as values stored in the memory 125 (or cache or memory of a processor 130) of the various apparatus 100, 100C, 100F or monitor 250, 250A embodiments. For example and without limitation, in a selected embodiment, in the presence of a battery, the magnetic field strengths measured with the Hall effect sensors 110 are typically between about 2-5 milligauss, and a first predetermined threshold (252) may be set at about 0.5 to one (1) milligauss. Also for example and without limitation, in a selected embodiment, in the presence of a magnet, the magnetic field strengths measured with the Hall effect sensors 110 are typically between about 15-50 milligauss, and a second predetermined threshold (254) may be set at about 8-10 milligauss.

There are innumerable ways to determine if the magnitude (e.g., amplitude) or variance of the target magnetic field measurements (compared to the reference or calibrated magnetic field magnitude (or strength)) is greater than a first (252) or second (254) predetermined threshold. For example, the maximum (or one or more maxima) 259, 261 of the target magnetic field magnitude (or strength) measurements may be compared to the first (252) or second (254) predetermined threshold, such as by determining whether the maximum (or one or more maxima) of the target magnetic field magnitude (or strength) measurements is greater than or equal to the first (252) or second (254) predetermined threshold, or by determining whether a difference between the maximum (or one or more maxima) of the target magnetic field magnitude (or strength) measurements and the first (252) or second (254) predetermined threshold is greater than zero. Also for example, one or more gradients of the target magnetic field magnitude (or strength) measurements may be compared to the first (252) or second (254) predetermined threshold, such as by determining whether the one or more gradients of the target magnetic field magnitude (or strength) measurements is greater than or equal to the first (252) or second (254) predetermined threshold.

In the second method 600, determining or calculating the difference between the two traces or plots, the target magnetic field magnitude (or strength) measurements versus the reference magnetic field magnitude (or strength) measurements, allows the identification of a battery or magnet. In the second method 600, a battery or a magnet is present if a sign reversal occurs in the differences between the reference and target magnetic field measurements (illustrated as 260, 265 in FIGS. 26 and 27), or in the differences between the gradients of the reference and target magnetic field measurements (step 635).

For the third representative battery and magnet detection apparatus 200-200D embodiments, also referred to equivalently as an "adhesive strip apparatus", also to quantify the magnetic field along the subject's body, several variations are also available, utilizing any of the apparatus 200A-200D embodiments. Referring to FIGS. 8 and 9, each of the apparatus 200A-200D embodiments comprises a housing 105B, which is generally embodied as a flexible material layer 274, which houses electronic components having either the second or third circuitry configurations 102, 103 (typically without an additional, optional sensor such as thermal sensor 235, although any such additional sensors may be included, if necessary or desirable in a selected embodiment). An adhesive layer (or film) 220 is coupled to or integrated with the flexible material layer 274 forming the housing 105B, and is covered by a removable cover 272. The removable cover 272 is removed to expose the adhesive layer 220 and attach one or more of the apparatus 200A-200D embodiments to the subject's body. As illustrated in FIGS. 14-16, a plurality of Hall effect sensors 110 are arranged on or within the flexible material layer forming the housing 105B, generally as a linear array of Hall effect sensors 110, to provide a measure of the magnetic field at each Hall effect sensor 110 location 225 along most of the length of the flexible material layer 274 forming the housing 105B.

In one variation, two identical apparatus 200 embodiments are utilized, and are illustrated and separately designated as representative battery and magnet detection apparatuses 200A and 200B to distinguish their respective placement on the subject's body. Each apparatus 200A and 200B has an array of linearly aligned Hall effect sensors 110, and are adhered to the subject's body, as illustrated in FIG. 20. The wireless version, apparatus 200D, may also be utilized identically, with two apparatuses 200D placed respectively in the same locations as the illustrated apparatuses 200A and 200B. The third representative battery and magnet detection apparatuses 200A and 200B may have the same or different form factors in length or width. The first adhesive strip apparatus 200A is placed and adhered over the first region or location 218 (indicated with an arrow), which is generally over (anterior to) the esophagus of the subject, such as beginning at the tip of the subject's chin 222 and extending to the distal end of the sternum, generally around the xiphoid process 224, as mentioned above as the first trace location, to provide the target magnetic field magnitude (or strength) measurements. The second adhesive strip apparatus 200B provides the baseline or reference measurements, and is placed generally over a second region or location 226 (also indicated with an arrow) of the subject's body 228, which is spaced-apart laterally and parallel to the first apparatus 200A, also over the chest or the side of the subject's chest, generally from the clavicle across the nipple region and extending distally from the nipple region, as mentioned above as the second trace location and illustrated as region 226 in FIG. 20, for example and without limitation. The generally linear array of Hall effect sensors 110 provide a measure of the magnetic field magnitude (or strength) at each Hall effect sensor 110 location 225, which are coupled over regions 218 and 216 of the subject's body.

In another variation, one apparatus 200C embodiment, having two spaced-apart arrays of linearly aligned Hall effect sensors 110, is adhered to the subject's body, as illustrated in FIG. 21, with Hall effect sensor 110 array 242 of apparatus 200C being placed and adhered over the first region or location 218, to provide the target magnetic field magnitude (or strength) measurements, and further with Hall effect sensor 110 array 244 of apparatus 200C being placed generally over a third region or location, spaced-apart inferiorly from the first region or location 218, illustrated as region 232 in FIGS. 20 and 21, for example and without limitation, to provide the reference magnetic field magnitude (or strength) measurements. The two generally linear arrays of Hall effect sensors 110 also provide a measure of the magnetic field magnitude (or strength) at each Hall effect sensor 110 location 225, which are coupled over regions 218 and 232 of the subject's body.

It should be noted that the wireless version of the apparatus 200, as apparatus 200D, may be utilized in any of these methods and variations and substituted for apparatus 200A, 200B, and/or 200C.

Referring to FIG. 11, using the first circuitry configuration 101 for the first, second, and fourth representative battery and magnet detection apparatus 100, 100C, 100F embodiments, the first, second, and fourth representative battery and magnet detection apparatus 100, 100C, 100F embodiments comprise at least one Hall effect sensor 110 which generates a Hall effect voltage signal (typically an analog signal), and generally a plurality of Hall effect sensors 110 arranged in a housing 105, 105A, 105C, such as arranged at the tip 185 of a housing 105, 105A, 105C, having a generally cylindrical and/or frustoconical form factor suitable for being portable and for being held in a person's hand, such as the illustrated hand-held, generally cylindrical "wand" apparatus 100, 100A, 100B, 100F, 100G, 100H, or such as arranged within the housing 105A having a generally cylindrical and/or disc form factor also suitable for being portable and for being held in a person's hand, such as the illustrated hand-held, generally disc-shaped apparatus 100C, 100D, 100E. Three Hall effect sensors 110 are illustrated, as Hall effect sensors $110_1$, $110_2$, and $110_3$, which are arranged orthogonally with respect to each other, to detect a magnetic field through any of three corresponding orthogonal directions, e.g., along any of three orthogonal planes formed by the x, y, and z axes. The orientation of each of the Hall effect sensors 110 covers the three planes of a three dimensional space. Thus, at least one of the Hall effect sensors 110 apparatus 100 will have a better or best orientation for detection of any magnetic field which may be present, to maximize the detection response and likelihood of detection of a battery or magnet.

For the embodiments having the first circuitry configuration 101, each of the Hall effect sensors 110 is coupled as an option to a filter 195, to reduce any noise by filtering, such as implementing a low pass filter to reduce any higher frequency noise (such as any signal greater than 50-100 Hz), and further coupled either through the filter 195 (when implemented) or directly to an amplifier 115, to amplify the (filtered) Hall effect voltage signal provided by the Hall effect sensors 110. The resulting amplified (or filtered and amplified) Hall effect voltage signal is provided to one or more analog-to-digital ("A/D") converters 120, to sample (e.g., at a 1-10 kHz sampling rate) and convert the analog amplified Hall effect voltage signal(s) to a plurality of corresponding digital Hall effect voltage values. The corresponding digital Hall effect voltage values are provided to a processor 130 and potentially also stored or otherwise recorded in a memory 125 (or cache or memory of a processor 130). It should be noted that in the event the processor 130 is implemented as an analog processor, then the conversion of the analog amplified Hall effect voltage signal(s) to a plurality of corresponding digital Hall effect voltage values is no longer necessary, and any A/D converter 120 also becomes unnecessary and may be omitted, for any of the embodiments described herein. The processor 130 will compare the target magnetic field measurements, as corresponding target magnetic field digital values, to the reference or baseline field (calibration) measurements, as corresponding reference magnetic field digital values, as described above and described in greater detail below. Depending upon the results of this comparison, such as when the presence of a battery or magnet has been determined or is likely, the processor 130 will generate a corresponding detection signal provided to one or more indicator(s) 140, such as visual or sound indicators, e.g., LEDs, speakers, etc., which provide a notification to medical or other treatment personnel or parent that a battery or magnet has been detected or has not been detected.

For example and without limitation, a sound may be emitted and/or an LED having a predetermined color may be turned on, either or both of which provide a notification or an alarm to medical or other treatment personnel or parent that a battery or magnet has been detected or is likely to be present (or has not been detected). Also for example and without limitation, the one or more indicator(s) 140 may be an addressable display, such as to display "a magnet is present", or "a battery may be present", or "a battery or magnet may be present and emergency attention is required", or "a battery may be present so please go to the emergency room immediately". As an option, a network interface ("I/F") 135 may also be included, such as for providing the corresponding detection signal to another form of display, such as a separate medical monitor. Also as illustrated, the first, second, and fourth representative battery and magnet detection apparatus 100, 100C, 100F embodiments also generally include a power supply (or source) 150, such as a battery which is optionally surrounded by a shield 160 to limit any field emitted by the power supply 150 from interfering with detection of an ingested battery or magnet, and may also include an optional voltage regulator 145, providing power to the various components via power rails 155. Alternatively, any such field generated by the power supply (or source) 150 will tend to be consistent between the reference or baseline field measurements and the target magnetic field measurements, and may be accounted for via a calibration, for example. The various components may be implemented as known in the electronic arts. For example and without limitation, the Hall effect sensors 110 for any of the various embodiments may be implemented using Hall effect sensor ICs (e.g., DRV5053 from Texas Instruments, for example and without limitation).

Referring to FIG. 12, a second circuitry configuration 102 is illustrated for the first, second, third, and fourth representative battery and magnet detection apparatus 100A, 100D, 100G, 200A, 200B, 200C embodiments, a first monitor 250 embodiment, and a first representative battery and magnet detection system 300 embodiment. For these embodiments, either only the one or more Hall effect sensors 110 or only the one or more Hall effect sensors 110, the optional filter 195, and the amplifier(s) 115 are provided in the housing 105, 105A, 105B, 105C, which may also include one or more input-output ("I/O") connectors 210, to provide wired communication to a second device, referred to as a monitor 250. A representative I/O connector 210A is illustrated in FIGS. 6 and 10 as a USB connector, as a representative option for any of the apparatus 100A, 100D, 100G, 200A, 200B, 200C embodiments having the second circuitry configuration 102 (and for purposes of clarification, such an I/O connector 210, 210A would not be present in the apparatus 100, 100C, 100F, 200C embodiments). The monitor 250 and the first, second, third, and fourth representative battery and magnet detection apparatus 100A, 100D, 100G, 200A, 200B, 200C embodiments together form a system 300 embodiment, and function as described above and below. The monitor 250 comprises the A/D converter(s) 120, processor 130, memory 125, indicator(s) 140, power supply 150 (and optional voltage regulator 145 and shielding 160) and optional network I/F 135, along with corresponding I/O connectors 215 to complete the wired connection(s) (such as via cables or busses 230, illustrated in FIG. 17) to the apparatus 100A, 100D, 100G, 200A, 200B, 200C embodiments (via I/O connector(s) 210). If not included in the apparatus 100A, 100D, 100G, 200A, 200B, 200C embodiments, the monitor 250 may also comprise the optional filter 195 and/or amplifier(s) 115 (which are then coupled (via I/O connectors 215, 210 directly to the one or more Hall effect sensors 110 of the apparatus 100A, 100D, 100G, 200A, 200B, 200C embodiments). In representative embodiments, as illustrated in FIG. 19, the monitor 250 is implemented as a separate device having a housing 270, such as a computer, tablet computer, smartphone, a docking station, or as described below, for example and without limitation, and may be coupled either to the Hall effect sensors 110 directly or coupled via the amplifier(s) 115 and optional filter 195, such as via one or more wires (230) and through corresponding I/O connectors 215, 210 or through a wireless connection (e.g., Bluetooth or the other data transmission protocols described below), illustrated and discussed below with reference to FIG. 13. The I/0 connectors 210, 215 are described in greater detail below. The system 300 functions exactly as described above with reference to the apparatus 100, 100C, 100F embodiments, differing only with respect to (a) the components and functionality being distributed among two physical devices (monitor 250 and apparatus 100A, 100D, 100G, 200A, 200B, 200C embodiments); (b) with communication from the amplifier(s) 115 to the A/D converter(s) 120 occurring via the I/O connectors 210, 215 and any intervening wired connections such as cables or busses 230 rather than directly via bus 231; and (c) with power provided to the apparatus 100A, 100D, 100G, 200A, 200B, 200C from the monitor 250 via the I/O connectors 210, 215 and any intervening wired connections such as cables or busses 230 rather than directly via power lines 155. For example, an indication that a battery or magnet may be present can be displayed on an indicator 140 of the monitor 250 (rather than of the apparatus 100, 100C, 100F), which may be embodied, for example, as a monitor display 141.

Referring to FIG. 13, a third circuitry configuration 103 is illustrated for the first, second, third, and fourth representative battery and magnet detection apparatus 100B, 100E, 100H, 200D embodiments, a second monitor 250A embodiment, and a second representative battery and magnet detection system 400 embodiment. For these embodiments, the one or more Hall effect sensor(s) 110, the optional filter 195, the amplifier(s) 115, and at least one wireless interface ("I/F") circuit 190 are provided in the housing 105, 105A, 105B, 105C, to provide wireless communication to another (third) device, referred to as a monitor 250A (e.g., Bluetooth or the other data transmission protocols described below). The third circuitry configuration 103 may also include a power supply 150A, or power may be provided through the wireless interface circuit 190. Depending on the wireless communication protocol to be implemented, such as whether digital rather than analog values are needed, the third representative battery and magnet detection apparatus 100B, 100E, 100H, 200D embodiments may further comprise one or more A/D converter(s) 120, as illustrated. The monitor 250A and the first, second, third, and fourth representative battery and magnet detection apparatus 100B, 100E, 100H, 200D embodiments together form the system 400 embodiment, and function as described above and below. The monitor 250A comprises the processor 130, the memory 125, the indicator(s) 140, optional network I/F 135, along with a corresponding wireless interface circuit 190 to complete the wireless communication connection to the corresponding apparatus 100B, 100E, 100H, 200D. If these components have not been included in the apparatus 100B, 100E, 100H, 200D embodiments, then the monitor 250A will also comprise any of the A/D converter(s) 120, optional filter 195 and amplifier(s) 115. In representative embodiments, as illustrated in FIG. 18, the monitor 250A is also implemented as a separate device having a housing 270, such as a computer, tablet computer, smartphone, a docking station, for example and without limitation, and also may be coupled to the Hall effect sensors 110 or the amplifiers 115 directly, such as through a wireless interface circuit 190, as mentioned above. The system 400 functions exactly as described above with reference to the apparatus 100, 100C, 100F embodiments, also differing only with respect to (a) the components and functionality being distributed among two physical devices (monitor 250A and apparatus 100B, 100E, 100H, 200D embodiments); (b) with communication from the amplifier(s) 115 or the A/D converter(s) 120 to the processor 130 occurring via the wireless interface circuits 190 rather than directly via bus 233; and (c) with power provided to the apparatus 100B, 100E, 100H, 200D from either a power supply 150A or from the monitor 250 via the wireless interface circuits 190 rather than directly via power lines 155. Also for example, an indication that a battery or magnet may be present can be displayed on an indicator 140 of the monitor 250 (rather than of the apparatus 100, 100C, 100F), which may be embodied, for example, as a monitor display 141.

Any of these various first, second, and third circuitry configurations 101, 102, 103, as an option, may also include a thermal sensor 235, which generates a temperature signal, which also may be filtered (filter 195), amplified (amplifier (s) 115), and converted to a digital value (or converted directly from the thermal sensor 235 to a digital value, as indicated by the dashed lines) (using A/D converter(s) 120), as described above, with the resulting digital temperature value(s) also provided to the processor 130 and potentially also stored in the memory 125 (or cache or memory of a processor 130). For example, as illustrated in FIG. 10, one or more thermal sensors 235 is or are arranged in the second tip 186 of the housing 105C, also forming a thermometer 205. The processor generates a corresponding temperature signal provided to one or more indicator(s) 140, and the resulting temperature may be displayed on the indicator(s) 140, or any other form of notification or indication provided, such as a sound of flashing light for a temperature above a threshold, such as above 99-100 degrees Fahrenheit, for example and without limitation.

For all of these various embodiments, using software or other programming instructions provided for the processor 130, the corresponding reference magnetic field digital values and the corresponding target magnetic field digital values are stored in the memory 125 (or cache or memory of a processor 130). The processor 130 may calculate averages and standard deviations of all measurements. It will also compare the stored target magnetic field digital values to the stored reference digital values, or compare them in real time. Here, the resulting reference or calibration values can be the average of all the reference measurements (i.e., the average or arithmetic mean of the corresponding reference digital values, the average or arithmetic mean of the power of the corresponding reference digital values from the Hall effect voltage signal, and may further account for any variance of the reference measurements). During one measurement cycle, for example and without limitation, up to 100 measurement points can be acquired. In case a sequence of target measurement points show a magnetic field variation greater than either first (252) or second (254) threshold levels, or in case the difference between target and reference measurements shows a sign reversal, as discussed in greater detail below, the presence of a battery or a magnet is indicated. A corresponding alarm or other warning can be issued by the processor 130, such as the detection signal provided to the indicator(s) 140, which for this embodiment, such indicator (s) 140 may be implemented as the display of monitor 250, 250A, such as the display of the computer or smartphone, as mentioned above, also for example and without limitation. Other types of models, such as models suitable for training, are discussed in greater detail below.

Referring to FIGS. 14-19, representative system 300A, 300B embodiments may comprise a monitor 250 and one or more third representative battery and magnet detection apparatus 200 embodiments, illustrated in FIG. 17 as third representative battery and magnet detection apparatuses 200A and 200B with a monitor 250 forming representative system 300A, or using a single apparatus 200C (arranged as shown in FIGS. 19 and 21) with a monitor 250 forming representative system 300B, which are coupled (through I/O connectors 210, 215) to the monitor 250, which may be arranged in a housing 270, such as having a form factor suitable for being portable and/or being held in a person's hand, such as illustrated in FIGS. 18 and 19. A representative system 400A embodiment may comprise a monitor 250A and one or more first, second, or fourth representative battery and magnet detection apparatus 100B, 100E, 100F embodiments, illustrated in FIG. 18, which has wireless communication to the monitor 250A, also which may be arranged in a housing 270, such as having a form factor suitable for being portable and/or being held in a person's hand. A representative system 400B embodiment may comprise a monitor 250A and one or more third representative battery and magnet detection apparatus 200D embodiments, illustrated in FIG. 18, which has wireless communication to the monitor 250A, also which may be arranged in a housing 270, such as having a form factor suitable for being portable and/or being held in a person's hand. Alternatively, the monitor 250, 250A may be provided within or as part of a larger computing or monitoring device configured or adapted to perform the methodology of the invention, as described above and in greater detail below, such as a smartphone, laptop, or computer having a processor 130 programmed to perform the functionality described herein.

The third representative battery and magnet detection apparatus 200-200D embodiments comprise a plurality of Hall effect sensors 110 arranged generally as a linear array, with each Hall effect sensor 110 positioned or arranged spaced apart from each other along a plurality of spaced-apart locations 225, on a housing 105B implemented as a flexible material layer or strip 274 which further has an adhesive film 220 on one side, for adhering one or more of the third representative battery and magnet detection apparatus 200-200D embodiments to the subject as shown in FIGS. 20 and 21. The flexible material layer 274 forming the housing 105B and the adhesive film 220 are each comprised of a biocompatible material suitable for adhering to the skin of a subject's body, as known or becomes known in the art, for example and without limitation. In one embodiment, a single Hall effect sensor 110 is utilized at each sensor location 225. In another embodiment, three Hall effect sensors 110 are utilized at each sensor location 225, e.g., Hall effect sensors $110_1$, $110_2$, and $110_3$, which are also arranged orthogonally with respect to each other, to detect a magnetic field through any of three corresponding orthogonal directions as described above, e.g., along x, y, and z axes. Each of the Hall effect sensors 110 is also coupled to an optional filter 195 and then to one or more amplifiers 115 (or coupled directly to one or more amplifiers 115), to filter and amplify or just amplify the Hall effect voltage signal provided by each of the Hall effect sensors 110, which corresponding (filtered and) amplified Hall effect voltage signals are then provided as an output from the third representative battery and magnet detection apparatus 200-200D embodiments, using I/O connectors 210 or wireless interface circuit 190. Alternatively, the optional filter 195 and the one or more amplifiers 115 may be provided in the monitor 250, 250A (not separately illustrated), and the Hall effect voltage signals may be provided directly to the I/O connectors 210 or wireless interface circuit 190. Depending on the protocol to be implemented by the wireless interface circuit 190, one or more A/D converters may also be included in an apparatus 200D embodiment.

Referring to FIG. 15, for an apparatus 200C embodiment, two arrays 242, 244 of Hall effect sensors 110 are provided on or in the flexible material layer 274 forming the housing 105B, which are spaced apart from each other by a predetermined distance, combining the functionality of two apparatus 200A and 200B embodiments into a single apparatus 200C. The first Hall effect sensor array 242 is arranged over the region 218 of the subject, to provide the target magnetic field measurements, while the second Hall effect sensor array 244 is arranged over the region 232 of the subject, to provide the reference or baseline magnetic field measurements, and otherwise functions as described above and below for any of the various apparatus 200, 200A, 200B, 200D embodiments. Although not separately illustrated, it should be noted that an apparatus 200D may also be implemented in this 200C apparatus configuration, substituting a wireless interface circuit 190 for the I/O connector 210, and possibly also including one or more A/D converters as previously described.

Reading from each of the Hall effect sensors 110 may be made continuously or sequentially, depending upon the selected embodiment. For example, in a representative third representative battery and magnet detection apparatus 200-200D embodiment, sixteen Hall effect sensors 110 are utilized at sixteen corresponding, spaced-apart locations 225. The corresponding Hall effect voltage signals may be filtered using optional filter 195 and sampled sequentially by the one or more amplifiers 115, and the corresponding filtered and amplified Hall effect voltage signals are then provided as a sequential output from the representative battery and magnet detection apparatus 200-200D embodiment, using I/O connectors 210 for wired data transfer or using wireless interface circuit 190 for wireless data transfer.

The I/O connectors are coupleable, such as through wires or bus 230, to corresponding I/O connectors 215 of the monitor 250, to transmit the filtered and amplified Hall effect voltage signal or just the Hall effect voltage signal to the monitor 250. In representative embodiments, the I/O connector(s) 210, 215 may have mating physical and electrical couplings (such as USB ports, electrical jacks, etc.) for connections to the wires or bus 230, as known or becomes known in the art, and may include a wide variety of coupling functionality, such as USB coupling, JTAG coupling, PCIe coupling, general purpose I/O, input power, ground, etc., for example and without limitation.

For a system 400A, illustrated in FIG. 18, using an apparatus 200D, the corresponding Hall effect voltage signals also may be filtered using optional filter 195 and sampled sequentially by the one or more amplifiers 115, and the corresponding filtered and amplified Hall effect voltage signals are then provided to an A/D converter 120, as previously described, and the digital values are then encoded and transmitted wirelessly be the wireless interface 190, also as a sequential output from the second representative battery and magnet detection apparatus 200D embodiment, using wireless data transfer. As mentioned above, depending on the selected embodiment, the (filtered and) amplified Hall effect voltage signals of just the Hall effect voltage signals may be transmitted wirelessly directly be the wireless interface 190.

Within the monitor 250, 250A, unless one or more A/D converters 120 were also included in the apparatus 100A, 100B, 100D, 100E, 100G, 100H, 200-200D embodiments, the filtered and amplified Hall effect voltage signals are also provided to one or more A/D converters 120, to sample and convert the analog amplified Hall effect voltage signals to a plurality of corresponding digital values. The corresponding digital values are provided to a processor 130 and potentially also stored in the memory 125 (or cache or memory of a processor 130). The processor 130 will compare the target magnetic field measurements, e.g., provided by the third representative battery and magnet detection apparatus 200A (or other apparatus 200C or 200D arranged in region 218), as corresponding target magnetic field digital values, to the reference or baseline field measurements provided by the third representative battery and magnet detection apparatus 200B (or other apparatus 200C or 200D arranged in region 226 or 232), as corresponding reference digital values, as described above and in greater detail below. Depending upon the results of this comparison, such as when the presence of a battery or magnet has been determined, the processor 130 can generate a corresponding detection signal provided to one or more indicator(s) 140, such as visual or sound indicators, e.g., LEDs, speakers, etc., which provide a notification to medical or other treatment personnel that a battery or magnet has been detected, as described above. For example, a sound may be emitted and/or an LED having a predetermined color may be turned on, either or both of which provide a notification or an alarm to medical or other treatment personnel that a battery or magnet has been detected, as mentioned above. As an option, a network interface ("I/F") 135 may also be included, such as for providing the corresponding detection signal to another form of display, such as a medical monitor. Also as illustrated, the monitor 250, 250A embodiment also generally includes a power supply (or source) 150, such as a battery surrounded by an optional shield 160 to prevent any field emitted by the power supply 150 from interfering with detection of an ingested battery or magnet, and may also include a voltage regulator 145, providing power to the various components via power rails 155A and 155B (via I/O connectors 210, 215 or via wireless interface circuit 190, for example). When the monitor 250, 250A is arranged a sufficient distance away from the apparatus 200-200D embodiments, such shielding 160 may be unnecessary, or may be accounted for in any calibration procedure, as mentioned above. The various components may be implemented as known in the electronic arts. As mentioned above, for example and without limitation, the Hall effect sensors 110 for any of the various embodiments may be implemented using Hall effect sensor ICs (e.g., DRV5053 from Texas Instruments, also for example and without limitation).

For example, the monitor 250, 250A having the one or more A/D converter(s) 120, processor 130, memory 125, indicator(s) 140, and optional network I/F 135 may be embodied in another device such as a computer, docking station, tablet or smart phone, for example and without limitation, and may be coupled directly to the amplifiers 115 or Hall effect sensors 110, such as via one or more wires 230 as illustrated, or through a wireless connection, such as through wireless interface circuit 190. Using software or other programming instructions provided for the processor 130, the corresponding reference digital values provided by the second representative battery and magnet detection apparatus 200B (or other apparatus 200C or 200D arranged in region 226 or 232) and the corresponding target magnetic field digital values provided by the second representative battery and magnet detection apparatus 200A (or other apparatus 200C or 200D arranged in region 218) are stored in the memory 125 (or cache or memory of a processor 130). The processor 130 may calculate averages and standard deviations of all measurements. It will also compare the stored target magnetic field digital values to the stored reference digital values, or compare them in real time. Here, the resulting reference or calibration values also can be the average of all the reference measurements (i.e., the average or arithmetic mean of the corresponding reference digital values, the average or arithmetic mean of the power of the corresponding reference digital values from the Hall effect voltage signal, and may further account for any variance of the reference measurements). During one measurement cycle, also or example and without limitation, up to 100 measurement points can be acquired. In case a sequence of target measurement points show a magnetic field variation greater than either first (252) or second (254) threshold levels, or in case the difference between target and reference measurements shows a sign reversal, as discussed in greater detail below, the presence of a battery or a magnet is indicated. A corresponding alarm or other warning can be issued by the processor 130, such as the detection signal provided to the indicator(s) 140, which for this embodiment, such indicator(s) 140 may be implemented as the display of monitor 250, 250A, such as the display of the computer or smartphone, as mentioned above, also for example and without limitation. Other types of models, such as models suitable for training, are discussed in greater detail below.

It should also be noted that any of the various apparatus 100 embodiments may also be combined, in a unitary package, with a second device or as part of a kit, such as a first aid kit. For example and as mentioned above, a fourth representative, hand-held battery and magnet detection apparatus 100F, 100G, 100H embodiment having one or more thermal sensors 235 forming a thermometer 205 is an example of a second device which may be integrated within any of the apparatus 100-100H embodiments.

Depending upon the embodiment, additional features may also be implemented in any of the apparatus 100, 200 embodiments, monitor 250, 250A embodiments, and system 300, 400 embodiments, including sophisticated modeling. For example, reference and target magnetic field measurements may be used as a feature vector to train a corresponding model. Feature extraction may be utilized with repeated sets of either or both reference and target magnetic field measurements. One or more feature vectors may be extracted, such as using a processor 130, and utilized to train any of the various apparatus 100, 200 embodiments, monitor 250, 250A embodiments, and system 300, 400 embodiments for increasingly accurate battery and magnet detection, including use of Bayesian prediction models, and across human age ranges and different types and sizes of animals. Such training can be performed and the resulting model included and stored in a memory 125 as part of device manufacture or distribution, for example and without limitation. As a result, small variations in target magnetic field measurements or values may still be utilized and be highly discriminatory to indicate the detection of a battery or magnet, for example.

FIG. 23 is a flow chart diagram illustrating a first representative method 500 embodiment, and provides a useful summary. The method begins, start step 505, as described above, with obtaining a magnetic field calibration or with reference or baseline magnetic field measurements being made, step 510, and with target magnetic field measurements being made, step 515, both using a representative apparatus 100-100H, 200-200D, alone or as part and/or system 300, 400 embodiment, to provide corresponding Hall effect voltage signals. The Hall effect voltage signals are then filtered (using optional filter 195) and amplified using one or more amplifiers 115, step 520, and converted to digital magnetic field values (using A/D converter(s) 120, and optionally stored in a memory 125 (or cache or memory of a processor 130), step 525. Depending on the selected embodiment, the amplified Hall effect voltage signals or digital magnetic field values also may be transmitted to a monitor 250, 250, in either step 520 or 525. Using a processor 130, the target magnetic field digital values are compared to a first predetermined threshold, step 530, and to a second predetermined threshold, step 540. When the target magnetic field digital values are less than the first predetermined threshold in step 530, the processor 130 generates a signal (e.g., to indicator(s) 140) to indicate that a battery or magnet has not been detected, step 535. When one or more of the target magnetic field digital values (e.g., any target magnetic field digital values, or a maxima 259, 261 of the target magnetic field digital values, or an average, mean or variance of the target magnetic field digital values) are greater than or equal to the first predetermined threshold in step 530, but less than the second predetermined threshold in step 540, the processor 130 generates a signal (e.g., to indicator(s) 140) to indicate that a battery has been or may have been detected, step 545. When one or more of the target magnetic field digital values (e.g., any target magnetic field digital values, or a maxima 259, 261 of the target magnetic field digital values, or an average, mean or variance of the target magnetic field digital values) are greater than or equal to the first predetermined threshold in step 530, and are greater than or equal to the second predetermined threshold in step 540, the processor 130 generates a signal (e.g., to indicator(s) 140) to indicate that a magnet has been or may have been detected, step 550. Following the indication steps 535, 545 and 550, the method may end, return step 555, or may be repeated as necessary or desirable, returning to start step 505 and iterating.

FIG. 24 is a flow chart diagram illustrating a second representative method 600 embodiment and also provides a useful summary. The method begins, start step 605, as described above, with obtaining a magnetic field calibration or with reference or baseline magnetic field measurements being made, step 610, and with target magnetic field measurements being made, step 615, both using a representative apparatus 100-100H, 200-200D, alone or as part and/or system 300, 400 embodiment, to provide corresponding Hall effect voltage signals. The Hall effect voltage signals are then filtered (using optional filter 195) and amplified using one or more amplifiers 115, step 620, and converted to digital magnetic field values (using A/D converter(s) 120, and optionally stored in a memory 125 (or cache or memory of a processor 130), step 625. Depending on the selected embodiment, the amplified Hall effect voltage signals or digital magnetic field values also may be transmitted to a monitor 250, 250, in either step 620 or 625. Using a processor 130, one or more differences are obtained between the target magnetic field digital values and corresponding reference target magnetic field digital values, step 630, such as calculating a difference between target and reference magnetic field values for each measurement point or location. When any of a plurality of differences between the target and reference magnetic field digital values shows a sign reversal or change in sign, step 635, the processor 130 generates a signal (e.g., to indicator(s) 140) to indicate that a battery or magnet has been or may have been detected, step 640. When none of the plurality of differences between the target and reference magnetic field digital values shows a sign reversal or change in sign, step 635, the processor 130 generates a signal (e.g., to indicator(s) 140) to indicate that a battery or magnet has not been detected, step 645. Following the indication steps 640 and 645, the method may end, return step 650, or may be repeated as necessary or desirable, returning to start step 605 and iterating.

Referring to FIGS. 26 and 27, tests have been conducted in three human cadavers. A coin (a U.S. quarter, as a non-magnetic object providing a control), and also no foreign body, were placed in the esophagus of the cadaver, and in both cases, a wand having a gauss meter was used to measure the magnetic field to provide the reference or baseline field measurements. A 20 mm button battery was placed in the esophagus of the cadaver and a wand having a gauss meter was used to measure the magnetic field to provide the target magnetic field measurements. For all cases, the wand was moved at a constant velocity from the face (nose and chin) to the xiphoid process of the sternum. Readings from the gauss meter were taken continuously, and readings at selected location were then plotted as shown in FIG. 26. Calculating the difference between the target magnetic field measurements made with the battery in place and the reference or baseline field measurements with either the control coin or no foreign body condition is shown in FIG. 27, with such calculations generally performed by a processor 130 in the representative embodiments. As indicated, the battery can be detected at the corresponding location in the esophagus, because of a sign difference or sign reversal (260 in FIG. 26, 265 in FIG. 27), at that location, resulting from the difference between the target magnetic field measurements and the reference or baseline field measurements, whereas there is no such sign difference or sign reversal, at any other locations, resulting from the difference between the target magnetic field measurements and the reference or baseline field measurements made at those locations. The presence of such as sign difference or sign reversal, in accordance with the representative embodiments, is utilized by the processor 130 as a positive indicator of the presence of a battery or magnet, with the issuance of a corresponding alarm or warning by the indicator(s) 140.

Equivalently, instead of a sign difference or sign reversal, a comparison of the gradients of the target magnetic field measurements and the reference or baseline field measurements may be utilized instead. A gradient of the target magnetic field measurements over a predetermined level (determined by the reference or baseline field measurements), in accordance with the representative embodiments, is utilized by the processor 130 as a positive indicator of the presence of a battery or magnet, with the issuance of a corresponding alarm or warning by the indicator(s) 140.

Numerous advantages of the representative embodiments are readily apparent. The representative apparatus, system and method provide for noninvasive detection of an ingested battery or magnet. The representative apparatus and system are comparatively unobtrusive, portable, convenient and easy to use for a treating physician, a nurse, a technician, other medical personnel, or an individual consumer, while nonetheless being comparatively or sufficiently accurate to obtain meaningful results and actionable information, with a comparatively fast detection time.

As used herein, a "processor" (or "controller") 130 may be any type of processor or controller, and may be embodied as one or more processor(s) 130 configured, designed, programmed or otherwise adapted to perform the functionality discussed herein. As the term processor or controller is used herein, a processor 130 may include use of a single integrated circuit ("IC"), or may include use of a plurality of integrated circuits or other components connected, arranged or grouped together, such as controllers, microprocessors, digital signal processors ("DSPs"), array processors, graphics or image processors, parallel processors, multiple core processors, custom ICs, application specific integrated circuits ("ASICs"), field programmable gate arrays ("FPGAs"), adaptive computing ICs, associated memory (such as RAM, DRAM and ROM), and other ICs and components, whether analog or digital. As a consequence, as used herein, the term processor or controller should be understood to equivalently mean and include a single IC, or arrangement of custom ICs, ASICs, processors, microprocessors, controllers, FPGAs, adaptive computing ICs, or some other grouping of integrated circuits which perform the functions discussed herein, with associated memory, such as microprocessor memory or additional RAM, DRAM, SDRAM, SRAM, MRAM, ROM, FLASH, EPROM or $E^2$PROM. A processor 130, with associated memory, may be adapted or configured (via programming, FPGA interconnection, or hard-wiring) to perform the methodology of the invention, as discussed herein. For example, the methodology may be programmed and stored, in a processor 130 with its associated memory (and/or memory 125) and other equivalent components, as a set of program instructions or other code (or equivalent configuration or other program) for subsequent execution when the processor 130 is operative (i.e., powered on and functioning). Equivalently, when the processor 130 may implemented in whole or part as FPGAs, custom ICs and/or ASICs, the FPGAs, custom ICs or ASICs also may be designed, configured and/or hard-wired to implement the methodology of the invention. For example, the processor 130 may be implemented as an arrangement of analog and/or digital circuits, controllers, microprocessors, DSPs and/or ASICs, collectively referred to as a "processor" or "controller", which are respectively hard-wired, programmed, designed, adapted or configured to implement the methodology of the invention, including possibly in conjunction with a memory 125.

The memory 125, which may include a data repository (or database), may be embodied in any number of forms, including within any computer or other machine-readable data storage medium, memory device or other storage or communication device for storage or communication of information, currently known or which becomes available in the future, including, but not limited to, a memory integrated circuit ("IC"), or memory portion of an integrated circuit (such as the resident memory within a processor 130 or processor IC), whether volatile or non-volatile, whether removable or non-removable, including without limitation RAM, FLASH, DRAM, SDRAM, SRAM, MRAM, FeRAM, ROM, EPROM or EPROM, or any other form of memory device, such as a magnetic hard drive, an optical drive, a magnetic disk or tape drive, a hard disk drive, other machine-readable storage or memory media such as a floppy disk, a CDROM, a CD-RW, digital versatile disk (DVD) or other optical memory, or any other type of memory, storage medium, or data storage apparatus or circuit, which is known or which becomes known, depending upon the selected embodiment. The memory 125 may be adapted to store various look up tables, parameters, coefficients, other information and data, programs or instructions (of the software of the present invention), and other types of tables such as database tables.

As indicated above, the processor 130 is hard-wired or programmed, using software and data structures of the invention, for example, to perform the methodology of the present invention. As a consequence, the system and related methods of the present invention may be embodied as software which provides such programming or other instructions, such as a set of instructions and/or metadata embodied within a non-transitory computer readable medium, discussed above. In addition, metadata may also be utilized to define the various data structures of a look up table or a database. Such software may be in the form of source or object code, by way of example and without limitation. Source code further may be compiled into some form of instructions or object code (including assembly language instructions or configuration information). The software, source code or metadata of the present invention may be embodied as any type of code, such as C, C++, Matlab, SystemC, LISA, XML, Java, Brew, SQL and its variations (e.g., SQL 99 or proprietary versions of SQL), DB2, Oracle, or any other type of programming language which performs the functionality discussed herein, including various hardware definition or hardware modeling languages (e.g., Verilog, VHDL, RTL) and resulting database files (e.g., GDSII). As a consequence, a "construct", "program construct", "software construct" or "software", as used equivalently herein, means and refers to any programming language, of any kind, with any syntax or signatures, which provides or can be interpreted to provide the associated functionality or methodology specified (when instantiated or loaded into a processor or computer and executed, including the processor 130, for example).

The software, metadata, or other source code of the present invention and any resulting bit file (object code, database, or look up table) may be embodied within any tangible, non-transitory storage medium, such as any of the computer or other machine-readable data storage media, as computer-readable instructions, data structures, program modules or other data, such as discussed above with respect to the memory 125, e.g., a floppy disk, a CDROM, a CD-RW, a DVD, a magnetic hard drive, an optical drive, or any other type of data storage apparatus or medium, as mentioned above.

The network interface 135 and wireless interface 190 are utilized for appropriate connection to a relevant channel, network or bus; for example, the network interface 135 may provide impedance matching, drivers and other functions for a wireline or wireless interface, may provide demodulation and analog to digital conversion for a wireless interface, and may provide a physical interface, respectively, for the computing device 132 and/or for the processor 130 and/or memory 125, with other devices. In general, the network interface 135 and wireless interface 190 are used to receive and transmit data, depending upon the selected embodiment, such as program instructions, parameters, configuration information, control messages, data and other pertinent information.

The various optional filter 195, amplifier(s) 115, and one or more A/D converters 120 all may be implemented as known or may become known in the art.

The network interface 135 and wireless interface 190 may be implemented as known or may become known in the art, to provide data communication between the processor 130 and any type of network or external device, such as wireless, optical, or wireline, and using any applicable standard (e.g., one of the various PCI, USB, RJ 45, Ethernet (Fast Ethernet, Gigabit Ethernet, 300ase-TX, 300ase-FX, etc.), IEEE 802.11, Bluetooth, WCDMA, WiFi, GSM, GPRS, EDGE, 3G and the other standards and systems mentioned above, for example and without limitation), and may include impedance matching capability, voltage translation for a low voltage processor to interface with a higher voltage control bus, wireline or wireless transceivers, and various switching mechanisms (e.g., transistors) to turn various lines or connectors on or off in response to signaling from processor 130. In addition, the network interface 135 and wireless interface 190 may also be configured and/or adapted to receive and/or transmit signals externally to the apparatus 100, 200 and/or system 300, 400, such as through hard-wiring or RF or infrared signaling, for example, to receive information in real-time for output on a display, for example. The network interface 135 and wireless interface 190 may provide connection to any type of bus or network structure or medium, using any selected architecture. By way of example and without limitation, such architectures include Industry Standard Architecture (ISA) bus, Enhanced ISA (EISA) bus, Micro Channel Architecture (MCA) bus, Peripheral Component Interconnect (PCI) bus, SAN bus, or any other communication or signaling medium, such as Ethernet, ISDN, T1, satellite, wireless, and so on.

The present disclosure is to be considered as an exemplification of the principles of the invention and is not intended to limit the invention to the specific embodiments illustrated. In this respect, it is to be understood that the invention is not limited in its application to the details of construction and to the arrangements of components set forth above and below, illustrated in the drawings, or as described in the examples. Systems, methods and apparatuses consistent with the present invention are capable of other embodiments and of being practiced and carried out in various ways.

Although the invention has been described with respect to specific embodiments thereof, these embodiments are merely illustrative and not restrictive of the invention. In the description herein, numerous specific details are provided, such as examples of electronic components, electronic and structural connections, materials, and structural variations, to provide a thorough understanding of embodiments of the present invention. One skilled in the relevant art will recognize, however, that an embodiment of the invention can be practiced without one or more of the specific details, or with other apparatus, systems, assemblies, components, materials, parts, etc. In other instances, well-known structures, materials, or operations are not specifically shown or described in detail to avoid obscuring aspects of embodiments of the present invention. In addition, the various Figures are not drawn to scale and should not be regarded as limiting.

Reference throughout this specification to "one embodiment", "an embodiment", or a specific "embodiment" means that a particular feature, structure, or characteristic described in connection with the embodiment is included in at least one embodiment of the present invention and not necessarily in all embodiments, and further, are not necessarily referring to the same embodiment. Furthermore, the particular features, structures, or characteristics of any specific embodiment of the present invention may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated. In addition, every intervening subrange within range is contemplated, in any combination, and is within the scope of the disclosure. For example, for the range of 5-10, the sub-ranges 5-6, 5-7, 5-8, 5-9, 6-7, 6-8, 6-9, 6-10, 7-8, 7-9, 7-10, 8-9, 8-10, and 9-10 are contemplated and within the scope of the disclosed range.

It will also be appreciated that one or more of the elements depicted in the Figures can also be implemented in a more separate or integrated manner, or even removed or rendered inoperable in certain cases, as may be useful in accordance with a particular application. Integrally formed combinations of components are also within the scope of the invention, particularly for embodiments in which a separation or combination of discrete components is unclear or indiscernible. In addition, use of the term "coupled" herein, including in its various forms such as "coupling" or "couplable", means and includes any direct or indirect electrical, structural or magnetic coupling, connection or attachment, or adaptation or capability for such a direct or indirect electrical, structural or magnetic coupling, connection or attachment, including integrally formed components and components which are coupled via or through another component.

With respect to signals, we refer herein to parameters that "represent" a given metric or are "representative" of a given metric, where a metric is a measure of a state of at least part of the regulator or its inputs or outputs. A parameter is considered to represent a metric if it is related to the metric directly enough that regulating the parameter will satisfactorily regulate the metric. A parameter may be considered to be an acceptable representation of a metric if it represents a multiple or fraction of the metric.

Furthermore, any signal arrows in the drawings/Figures should be considered only exemplary, and not limiting, unless otherwise specifically noted. Combinations of components of steps will also be considered within the scope of the present invention, particularly where the ability to separate or combine is unclear or foreseeable. The disjunctive term "or", as used herein and throughout the claims that follow, is generally intended to mean "and/or", having both conjunctive and disjunctive meanings (and is not confined to an "exclusive or" meaning), unless otherwise indicated. As used in the description herein and throughout the claims that follow, "a", "an", and "the" include plural references unless the context clearly dictates otherwise. Also as used in the description herein and throughout the claims that follow, the meaning of "in" includes "in" and "on" unless the context clearly dictates otherwise.

The foregoing description of illustrated embodiments of the present invention, including what is described in the summary or in the abstract, is not intended to be exhaustive or to limit the invention to the precise forms disclosed herein. From the foregoing, it will be observed that numerous variations, modifications and substitutions are intended and may be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

The invention claimed is:

1. A system for detection of an ingested battery or magnet, the system comprising:
    a detection apparatus comprising:
        a plurality of Hall effect sensors to generate a corresponding plurality of Hall effect voltage signals; and
        an amplifier coupled to the plurality of Hall effect sensors to amplify the plurality of Hall effect voltage signals, and generate at least one first amplified Hall effect voltage signal provided as a calibration or reference magnetic field measurement and generate a second plurality of amplified Hall effect voltage signals provided as target magnetic field measurements.

2. The system of claim 1, further comprising:
    a monitor comprising:
        an analog-to-digital converter to receive the at least one first amplified Hall effect voltage signal and the second plurality of amplified Hall effect voltage signals and respectively convert the first amplified Hall effect voltage signal and second plurality of amplified Hall effect voltage signals to a corresponding calibration or reference magnetic field digital value and to corresponding target magnetic field digital values; and
        a processor coupled to the analog-to-digital converter, the processor adapted to compare one or more target magnetic field digital values with a first predetermined threshold, and when one or more target magnetic field digital values is greater than or equal to the first predetermined threshold, to generate a detection signal indicating the presence of an ingested battery or magnet.

3. The system of claim 2, wherein the processor is further adapted to compare the one or more target magnetic field digital values with the first predetermined threshold and with a second predetermined threshold, and when one or more target magnetic field digital values is greater than or equal to the first predetermined threshold and less than the second predetermined threshold, to generate a detection signal indicating the presence of an ingested battery.

4. The system of claim 3, wherein the processor is further adapted, when one or more target magnetic field digital values is greater than or equal to the second predetermined threshold, to generate a detection signal indicating the presence of an ingested magnet.

5. The system of claim 2, wherein the processor is further adapted to use at least one maximum or gradient of the one or more target magnetic field digital values to compare the one or more target magnetic field digital values with the first predetermined threshold.

6. The system of claim 2, wherein the system is portable.

7. The system of claim 2, wherein the monitor has a hand-held form factor.

8. The system of claim 2, wherein the monitor is embodied in a computer, a tablet computer, or a smartphone.

9. The system of claim 1, further comprising:
a monitor comprising:
an analog-to-digital converter to receive the at least one first amplified Hall effect voltage signal and the second plurality of amplified Hall effect voltage signals and respectively convert the first amplified Hall effect voltage signal and second plurality of amplified Hall effect voltage signals to a corresponding calibration or reference magnetic field digital value and to corresponding target magnetic field digital values; and
a processor coupled to the analog-to-digital converter, the processor adapted to determine one or more differences between the corresponding calibration or reference magnetic field digital value and the target magnetic field digital values, and when at least one difference has a sign reversal, to generate a detection signal indicating the presence of an ingested battery or magnet.

10. The system of claim 1, wherein the detection apparatus further comprises:
a filter coupled to the plurality of Hall effect sensors and to the amplifier to filter the plurality of Hall effect voltage signals; and
a housing having a hand-held, generally cylindrical or disc-shaped form factor; and
wherein the plurality of Hall effect sensors are arranged near a tip or center of the housing.

11. The system of claim 1, wherein the detection apparatus further comprises:
a filter coupled to the plurality of Hall effect sensors and to the amplifier to filter the plurality of Hall effect voltage signals; and
a housing comprising:
a flexible material layer; and
an adhesive coupled to the flexible material layer.

12. The system of claim 1, wherein the detection apparatus further comprises:
a thermal sensor.

13. A method of using the system of claim 1 for detection of an ingested battery or magnet in a human or animal subject, comprising:
moving or positioning the detection apparatus along a first region anterior to the esophagus of the subject to generate the target magnetic field measurements at one or more first locations; and
moving or positioning the detection apparatus in a second region spaced-apart from the first region, to generate the one or more calibration or reference magnetic field measurements at one or more second locations.

14. A method of using the system of claim 1 for detection of an ingested battery or magnet in a human or animal subject, comprising:
moving the detection apparatus along a first region anterior to the esophagus of the subject to generate the target magnetic field measurements at one or more first locations; and
calibrating the detection apparatus in a second region spaced-apart from the first region, to generate the one or more calibration or reference magnetic field measurements at one or more second locations.

15. An apparatus for detection of an ingested battery or magnet, the apparatus comprising:
at least one Hall effect sensor to generate a plurality of Hall effect voltage signals;
an amplifier coupled to the at least one Hall effect sensor to amplify the plurality of Hall effect voltage signals, and generate at least one first amplified Hall effect voltage signal provided as a calibration or reference magnetic field measurement and generate a second plurality of amplified Hall effect voltage signals provided as target magnetic field measurements;
an analog-to-digital converter to receive the first amplified Hall effect voltage signal and the second pluralities of amplified Hall effect voltage signals and respectively convert the first amplified Hall effect voltage signal and second plurality of amplified Hall effect voltage signals to a corresponding calibration or reference magnetic field digital value and corresponding target magnetic field digital values; and
a processor coupled to the analog-to-digital converter, the processor adapted to compare one or more target magnetic field digital values with a first predetermined threshold, and when one or more target magnetic field digital values is greater than or equal to the first predetermined threshold, to generate a detection signal indicating the presence of an ingested battery or magnet.

16. The apparatus of claim 15, wherein the processor is further adapted to compare the one or more target magnetic field digital values with the first predetermined threshold and with a second predetermined threshold, and when one or more target magnetic field digital values is greater than or equal to the first predetermined threshold and less than the second predetermined threshold, to generate a detection signal indicating the presence of an ingested battery.

17. The apparatus of claim 16, wherein the processor is further adapted, when one or more target magnetic field digital values is greater than or equal to the second predetermined threshold, to generate a detection signal indicating the presence of an ingested magnet.

18. The apparatus of claim 15, wherein the processor is further adapted to use at least one maximum or gradient of the one or more target magnetic field digital values to compare the one or more target magnetic field digital values with the first predetermined threshold.

19. The apparatus of claim 15, wherein the apparatus further comprises:

a filter coupled to the at least one Hall effect sensor and to the amplifier to filter the plurality of Hall effect voltage signals; and a housing having a hand-held, generally cylindrical form factor and wherein the plurality of Hall effect sensors are arranged near a tip of the housing.

20. The apparatus of claim 15, wherein the apparatus further comprises:

a filter coupled to the at least one Hall effect sensor and to the amplifier to filter the plurality of Hall effect voltage signals; and a housing having a hand-held, disc-shaped form factor and wherein the plurality of Hall effect sensors are arranged near a center of the housing.

21. The apparatus of claim 15, wherein the apparatus further comprises:

a thermal sensor.

22. A method of using the apparatus of claim 15 for detection of an ingested battery or magnet in a human or animal subject, comprising:

moving the detection apparatus along a first region anterior to the esophagus of the subject to generate the target magnetic field measurements at one or more first locations; and moving the detection apparatus in a second region spaced-apart from the first region, to generate one or more calibration or reference magnetic field measurements at one or more second locations.

23. A method of using the apparatus of claim 15 for detection of an ingested battery or magnet in a human or animal subject, comprising:

moving the detection apparatus along a first region anterior to the esophagus of the subject to generate the target magnetic field measurements at one or more first locations; and calibrating the detection apparatus in a second region spaced-apart from the first region, to generate one or more calibration or reference magnetic field measurements at one or more second locations.

24. A system for detection of an ingested battery or magnet, the system comprising:

a first detection apparatus comprising:

a first flexible strip having an adhesive film;

a first plurality of Hall effect sensors to generate a corresponding first plurality of Hall effect voltage signals, the first plurality of Hall effect sensors arranged as a linear array on or within the first flexible strip; and a first amplifier coupled to the first plurality of Hall effect sensors to amplify the first plurality of Hall effect voltage signals and generate a first plurality of amplified Hall effect voltage signals provided as reference magnetic field measurements; and a second detection apparatus comprising:

a second flexible strip having an adhesive film;

a second plurality of Hall effect sensors to generate a corresponding second plurality of Hall effect voltage signals, the second plurality of Hall effect sensors arranged as a linear array on or within the second flexible strip; and a second amplifier coupled to the second plurality of Hall effect sensors to amplify the second plurality of Hall effect voltage signals and generate a second plurality of amplified Hall effect voltage signals provided as target magnetic field measurements.

25. The system of claim 24, wherein each of the first and second detection apparatuses further comprise:

a filter coupled to the first or second plurality of Hall effect sensors and to the first or second amplifier to filter the first or second plurality of Hall effect voltage signals; and an input-output connector.

26. The system of claim 24, wherein each of the first and second detection apparatuses further comprise:

a filter coupled to the first or second plurality of Hall effect sensors and to the first or second amplifier to filter the first or second plurality of Hall effect voltage signals; and a wireless interface circuit.

27. The system of claim 24, further comprising:

a monitor comprising:

an analog-to-digital converter to receive the first and second pluralities of amplified Hall effect voltage signals and respectively convert the first and second pluralities of amplified Hall effect voltage signals to corresponding calibration or reference magnetic field digital values and target magnetic field digital values; and a processor coupled to the analog-to-digital converter, the processor adapted to compare one or more target magnetic field digital values with a first predetermined threshold, and when one or more target magnetic field digital values is greater than or equal to the first predetermined threshold, to generate a detection signal indicating the presence of an ingested battery or magnet.

28. The system of claim 27, wherein the processor is further adapted to compare the one or more target magnetic field digital values with the first predetermined threshold and with a second predetermined threshold, and when one or more target magnetic field digital values is greater than or equal to the first predetermined threshold and less than the second predetermined threshold, to generate a detection signal indicating the presence of an ingested battery.

29. The system of claim 28, wherein the processor is further adapted, when one or more target magnetic field digital values is greater than or equal to the second predetermined threshold, to generate a detection signal indicating the presence of an ingested magnet.

30. The system of claim 27, wherein the processor is further adapted to use at least one maximum or gradient of the one or more target magnetic field digital values to compare the one or more target magnetic field digital values with the first predetermined threshold.

31. The system of claim 27, wherein the system is portable.

32. The system of claim 27, wherein the monitor has a hand-held form factor.

33. The system of claim 27, wherein the monitor is embodied in a computer, a tablet computer, or a smartphone.

34. The system of claim 24, further comprising:

a monitor comprising:

an analog-to-digital converter to receive the first and second pluralities of amplified Hall effect voltage signals and respectively convert the first and second pluralities of amplified Hall effect voltage signals to corresponding calibration or reference magnetic field digital values and target magnetic field digital values; and a processor coupled to the analog-to-digital converter, the processor adapted to determine one or more differences between the corresponding calibration or reference magnetic field digital value and the target magnetic field digital values, and when at least one difference has a sign reversal, to generate a detection signal indicating the presence of an ingested battery or magnet.

35. A method of using the system of claim 24 for detection of an ingested battery or magnet in a human or animal subject, comprising:
   arranging the second detection apparatus in a first region anterior to the esophagus of the subject;
   arranging the first detection apparatus laterally and spaced-apart from the second detection apparatus in a second region along the chest or side of the subject; and
   providing power to the first and second detection apparatuses to generate the first and second pluralities of Hall effect voltage signals.

36. A non-invasive method of detecting an ingested battery or magnet in a human or animal subject, the method comprising:
   moving an apparatus having at least one Hall effect sensor along a first region of the subject to generate target magnetic field measurements at one or more first locations;
   calibrating the apparatus spaced apart from the first region or moving the apparatus in a second region of the human subject to generate reference magnetic field measurements at one or more second locations;
   comparing one or more target magnetic field measurements with a first predetermined threshold; and
   detecting the presence of an ingested battery or magnet when one or more target magnetic field digital values is greater than or equal to the first predetermined threshold.

37. The method of claim 36, further comprising:
   comparing the one or more target magnetic field digital values with the first predetermined threshold and with a second predetermined threshold; and
   detecting the presence of an ingested battery when one or more target magnetic field digital values is greater than or equal to the first predetermined threshold and less than the second predetermined threshold, to generate a detection signal indicating the presence of an ingested battery.

38. The method of claim 37, further comprising:
   detecting the presence of an ingested when one or more target magnetic field digital values is greater than or equal to the second predetermined threshold.

39. The method of claim 36, wherein the step of comparing further comprises:
   determining at least one maximum or gradient of the one or more target magnetic field digital values; and
   comparing the at least one maximum or gradient with the first predetermined threshold.

40. The method of claim 36, wherein the first region is anterior to the esophagus of the human subject.

41. The method of claim 36, wherein the first region extends between the tip of the chin to the xiphoid process of the subject.

42. The method of claim 36, wherein the second region is lateral to and spaced-apart from the first region.

43. The method of claim 36, wherein the second region is along the chest or side of the subject.

* * * * *